(12) United States Patent
Rau et al.

(10) Patent No.: US 12,324,797 B2
(45) Date of Patent: *Jun. 10, 2025

(54) THERAPEUTIC COMPOSITIONS

(71) Applicant: WINTERMUTE BIOMEDICAL, INC., Corvallis, MT (US)

(72) Inventors: Thomas F. Rau, Victoria (AU); Geoffrey W. Rogers, Fitzroy (AU)

(73) Assignee: Wintermute Biomedical, Inc., Corvallis, MT (US)

( * ) Notice: Subject to any disclaimer, the term of this patent is extended or adjusted under 35 U.S.C. 154(b) by 1050 days.

This patent is subject to a terminal disclaimer.

(21) Appl. No.: 17/282,185

(22) PCT Filed: Oct. 1, 2019

(86) PCT No.: PCT/US2019/054044
§ 371 (c)(1),
(2) Date: Apr. 1, 2021

(87) PCT Pub. No.: WO2020/072479
PCT Pub. Date: Apr. 9, 2020

(65) Prior Publication Data
US 2022/0000825 A1 Jan. 6, 2022

Related U.S. Application Data

(60) Provisional application No. 62/845,858, filed on May 9, 2019, provisional application No. 62/845,859, filed (Continued)

(51) Int. Cl.
*A61K 31/20* (2006.01)
*A01N 33/12* (2006.01)
(Continued)

(52) U.S. Cl.
CPC .............. *A61K 31/20* (2013.01); *A01N 33/12* (2013.01); *A01N 37/06* (2013.01); *A01N 37/44* (2013.01);
(Continued)

(58) Field of Classification Search
CPC .. A61K 31/201; A61K 9/0014; A61K 31/198; A61K 31/20; A61K 45/06;
(Continued)

(56) References Cited

U.S. PATENT DOCUMENTS 4,147,769 A * 4/1979 Dea ........................ A61Q 15/00
424/47
4,150,052 A 4/1979 Watson et al.
(Continued)

FOREIGN PATENT DOCUMENTS

CN 1969984 A 5/2007
CN 101991726 A 3/2011
(Continued)

OTHER PUBLICATIONS

Angele et al.; L-arginine: a unique amino acid for improving depressed wound immune function following hemorrhage; European Surgical Research; 34(1-2); pp. 53-60; Jan.-Apr. 2002.
(Continued)

*Primary Examiner* — Deborah D Carr
(74) *Attorney, Agent, or Firm* — Shay Glenn LLP

(57) ABSTRACT

Compositions of fatty acids (e.g., including one or more C4 to C40 fatty acids, such as a C4 to C20 fatty acid) and one or more amino acids (and particularly one or more amino acids having electrically charged basic side chains, e.g., Arginine, Lysine, etc.) for use as an anti-pathogenic composition. These compositions may find particular use as anti-bacterial and in some variations anti-viral, anti-fungal and anti-cancer compositions.

15 Claims, 18 Drawing Sheets

Related U.S. Application Data on May 9, 2019, provisional application No. 62/739,844, filed on Oct. 1, 2018.

(51) Int. Cl.

| | |
|---|---|
| *A01N 37/06* | (2006.01) |
| *A01N 37/44* | (2006.01) |
| *A61K 9/00* | (2006.01) |
| *A61K 31/198* | (2006.01) |
| *A61K 31/201* | (2006.01) |
| *A61K 45/06* | (2006.01) |
| *A61K 47/55* | (2017.01) |
| *A61P 31/02* | (2006.01) |
| *A61P 31/04* | (2006.01) |
| *A61K 31/14* | (2006.01) |

(52) U.S. Cl.
CPC .......... *A61K 9/0014* (2013.01); *A61K 31/198* (2013.01); *A61K 31/201* (2013.01); *A61K 47/55* (2017.08); *A61P 31/02* (2018.01); *A61P 31/04* (2018.01); *A61K 31/14* (2013.01); *A61K 45/06* (2013.01)

(58) Field of Classification Search
CPC ........ A61K 31/202; A61K 9/08; A61K 9/107; A61K 2300/00; A01N 37/06; A61P 31/04; A61P 31/12; A61P 31/22; A61P 35/00; A61L 27/54; A61L 29/16; A61L 31/16; A61L 2300/214; A61L 2300/22; A61L 2300/404

See application file for complete search history.

(56) References Cited

U.S. PATENT DOCUMENTS

| | | | |
|---|---|---|---|
| 5,260,066 | A | 11/1993 | Wood et al. |
| 5,766,614 | A | 6/1998 | Yong |
| 6,015,798 | A | 1/2000 | Ogilvie et al. |
| 6,696,081 | B2 | 2/2004 | Grinstaff et al. |
| 6,841,174 | B2 | 1/2005 | Shalaby et al. |
| 7,288,265 | B1 | 10/2007 | Rolf |
| 7,671,011 | B2 | 3/2010 | Shai et al. |
| 10,195,242 | B2 | 2/2019 | Hale et al. |
| 10,894,788 | B2 | 1/2021 | Kanouni et al. |
| 11,065,220 | B2 | 7/2021 | Weston et al. |
| 11,103,475 | B2 * | 8/2021 | Rau .................... A61P 31/22 |
| 2006/0159746 | A1 | 7/2006 | Troup et al. |
| 2007/0258913 | A1 | 11/2007 | Rossel |
| 2008/0026974 | A1 | 1/2008 | Barnhart et al. |
| 2008/0206159 | A1 | 8/2008 | Tamarkin et al. |
| 2008/0253973 | A1 * | 10/2008 | Tamarkin ............ A61K 8/8158 424/47 |
| 2009/0068128 | A1 | 3/2009 | Waddington |
| 2010/0111879 | A1 | 5/2010 | Tamarkin et al. |
| 2011/0034557 | A1 | 2/2011 | Jarrell et al. |
| 2012/0328544 | A1 | 12/2012 | Stockel et al. |
| 2016/0066578 | A1 | 3/2016 | Ala'Aldeen et al. |
| 2020/0230096 | A1 | 7/2020 | Rau et al. |
| 2020/0282067 | A1 | 9/2020 | Rau et al. |
| 2022/0040135 | A1 | 2/2022 | Rau et al. |

FOREIGN PATENT DOCUMENTS

| | | |
|---|---|---|
| CN | 102178842 A | 9/2011 |
| EP | 1842437 A1 | 10/2007 |
| EP | 1595936 B1 | 10/2011 |
| GB | 2051574 A | 1/1981 |
| JP | 11-269034 A | 10/1999 |
| JP | H11513561 A | 11/1999 |
| JP | 2000281528 A | 10/2000 |
| JP | 2002114670 A | 4/2002 |
| JP | 2008208059 A | 9/2008 |
| JP | 2009263231 A | 11/2009 |
| JP | 2013520398 A | 6/2013 |
| RU | 2356247 C2 | 5/2009 |
| WO | WO00/029025 A1 | 5/2000 |
| WO | WO2004/026840 A1 | 4/2004 |
| WO | WO2004/110341 A2 | 12/2004 |
| WO | WO2005/049553 A1 | 6/2005 |
| WO | WO2005/123101 A1 | 12/2005 |
| WO | WO2006/046025 A1 | 5/2006 |
| WO | WO2008/111532 A1 | 9/2008 |
| WO | WO2009/090648 A2 | 7/2009 |
| WO | WO2012/090205 A2 | 7/2012 |
| WO | WO2018/148763 A1 | 8/2018 |

OTHER PUBLICATIONS

Atilano et al.; Wall teichoic acids of *Staphylococcus aureus* limit recognition by the *Drosophila peptidoglycan* recognition protein-SA to promote pathogenicity; Plos Pathogens; 7(12); ; 13 pages; e1002421; Dec. 1, 2011.

Bourne et al.;Effect of Undecylenic Acid as a Topical Microbicide Against Genital Herpes Infection in Mince and Guinea Pigs; Antiviral Research; 40(3); pp. 139-144; Jan. 1, 1999.

Brown et al.; Methicillin resistance in *Staphylococcus aureus* requires glycosylated wall teichoic acids; Proceedings of the National Academy of Sciences: 109(46); pp. 18909-18914; (Author Manuscript); Nov. 13, 2012.

Brown et al.; *Staphylococcus aureus* and Bacillus subtilis W23 make polyribitol wall teichoic acids using different enzymatic pathways; Chemistry and Bilogy; 17(10); pp. 1101-1110; Oct. 29, 2010.

Chung et al.; Rhein affects arylamine N-acetyltransferase activity in Helicobacter pylori from peptic ulcer patients; Journal of Applied Toxicology; 18(2); pp. 117-123; Mar. 1, 1998.

Ding et al.; Screening for Novel Quorum-Sensing Inhibitors to Interfere with the Formation of Pseudomonas aeruginosa Biofilm; Journal of Medical Microbiology; 60(12); pp. 1827-1834; Dec. 1, 2011.

Diep et al.; Complete genome sequence of USA300, an epidemic clone of community-acquired meticillin-resistant *Staphylococcus aureus*; The Lancet; 367(9512); pp. 731-739; Mar. 4, 2006.

Diep et al.; The arginine catabolic mobile element and staphylococcal chromosomal cassette mec linkage: convergence of virulence and resistance in the USA300 clone of methicillin-resistant *Staphylococcus aureus*; The Journal of Infectious Diseases: 197(11); pp. 1523-1530; Jun. 1, 2008.

Drugs.com; Rhubarb; 8 pages; retrieved from the internet (https://www.drugs.com/npp/rhubarb.html) on May 8, 2018.

Garcia-Sosa et al.; Chrysophanol, an antimicrobial anthraquinone from the root extract of colubrina greggii; Journal of the Mexican Chemical Society; 50(2); pp. 76-78; Jun. 2006.

Green et al.; Nitric oxide: cytokine-regulation of nitric oxide in host resistance to intracellular pathogens; Immunology Letter; 43(1-2); pp. 87-94; Dec. 1, 1994.

Handa et al.; (Ed); Extraction technologies for medicinal and aromatic plants; United Nations Industrial Development Organization and the International Centre for Science and High Technology, Trieste: 266 pages; (year of pub. sufficiently earlier than effective US filing date and any foreign priority date); 2008.

Hatano et al.; Phenolic Constituents of Cassia Seeds and Antibacterial Effect of Some Naphthalenes and Anthraquinones on Methicillin-Resistant *Staphylococcus aureus*; Chemical and Pharmaceutican Bulletin; Pharmaceutical Society of Japan; 47(8); pp. 1121-1127; Jan. 1, 1999.

Helms et al.; Natural Treatment of Chronic Rhinosinusitis; Alternative Medicine Reviews; 11(3); pp. 196-207; Sep. 1, 2006.

Lai et al.; Rhein induced apoptosis through the endoplasmic reticulum stress, caspase- and mitochondria-dependent pathways in SCC-4 human tongue squamous cancer cells; In Vivo; 23(2); pp. 309-316; Mar. 1, 2009.

Lee et al.; Synergistic effect of emodin in combination with ampicillin or oxacillin against methicillin-resistant *Staphylococcus aureus*; Pharmaceutical Bilogy; 48(11); pp. 1285-1290; Nov. 1, 2010.

(56) References Cited

OTHER PUBLICATIONS

Li et al.; Potent In Vitro Antifungal Activities of Naturally-Occurring Acetylenic Acids; Antimicrobial Agents and Chemotherapy; 52(7); pp. 2442-2448; Jul. 1, 2008.
MacMicking et al.; Identification of nitric oxide synthase as a protective locus against tuberculosis; Proceedings of the National Academy of Sciences: 94(10); pp. 5243-5248; May 13, 1997.
MacMicking et al.; Nitric oxide and macrophage function; Annual Review of Immunology; 15(1); pp. 323-350; Apr. 15, 1997.
McLain et al.; Undecylenic Acid Inhibits Morphogenesis of Candida albicans; Antimicrobial Agents and Chemotherapy: 44(10); pp. 2873-2875; Oct. 1, 2000.
Mohamed et al.; Antibacterial activity of novel cationic peptides against clinical isolates of multi-drug resistant *Staphylococcus pseudintermedius* from infected dogs; PloS one; 9(12); 20 pages; DOI:10.1371/journal.pone.0116259; Dec. 31, 2014.
Monograph; Undecylenic Acid; , Alternative Medicine Review, 7(1); pp. 68-70; Feb. 2002.
Morris; Enzymes of arginine metabolism; The Journal of Nutrition; 134(10); pp. 2743S-2747S; Oct. 1, 2004.
Nakaki et al.; L-arginine-induced hypotension; The Lancet; 336(8716); pp. 696; Sep. 15, 1990.
Nelson; Undecylenic acid in the treatment of psoriasis and neurodermatitis; California Medicine; 74(1); pp. 17; Jan. 1951.
Rattner et al.; Treatment of psoriasis with undecylenic acid by mouth; Journal of the American Medical Association; 146(12); pp. 1113-1115; Jul. 21, 1951.
Seguin et al.; Induction of nitric oxide synthase protects against malaria in mice exposed to irradiated Plasmodium berghei infected mosquitoes: involvement of interferon gamma and CD8+ T cells; Journal of Experimental Medicine; 180(1); pp. 353-358; Jul. 1, 1994.
Shafran et al.; Topical undecylenic acid for herpes simplex labialis: a multicenter, placebo-controlled trial; Journal of Infectious Diseases; 176(1); pp. 78-83; Jul. 1, 1997.
Testa et al.; Hydrolysis in drug and prodrug metabolism: Chemistry, Biochemistry, and Enzymology; Wiley-VCH, Zurich, Switzerland, 2003; 11 pages; retrieved from the interent (http://sutlib2.sut.ac.th/sut_contents/H89132.pdf); on May 8, 2018.
Thurlow et al.; Functional Modularity of the Arginine Catabolic Mobil Element Contributes to the Success of USA300 Methicillin-Resistant *Staphylococcus aureus*; Cell Host and Microbe; 13(1); pp. 100-107; (Author Manuscript); Jan. 16, 2013.
Kosikowska et al.; Antimicrobial Activity and Total Content of Polyphenols or Rheum L. Species Growing in Poland; Central European Journal of Biology; 5(6); pp. 814-820; Dec. 1, 2010.
Wrong; Undecylenic acid administered orally in the treatment of psoriasis; Can. Med. Assoc. J . . .; 63(6); pp. 543-545; Dec. 1950.
Wu et al.; Antimicrobial properties and toxicity of anthraquinones by microcalorimetric bioassay; Chinese Journal of Chemistry; 24(1); pp. 45-50; Jan. 1, 2006.
Yu et al.; Global transcriptional response of *Staphylococcus aureus* to rhein, a natural plant product; Journal of Biotechnology; 135(3); pp. 304-308; Jun. 30, 2008.
Kharkevich; Pharmacology: Textbook; 10th edition; pp. 73; 2010 (the year of publication is sufficiently earlier than the effective U.S. filing date and any foreign priority date so that the particular month of publication is not in issue).
Kholodov et al.; Clinical pharmacokinetics, Medicine; pp. 83-98, 134-138m 160m 378-380; 1985 (the year of publication is sufficiently earlier than the effective U.S. filing date and any foreign priority date so that the particular month of publication is not in issue).
Sergeeva; A short course in molecular pharmacology; pp. 10; 1975 (the year of publication is sufficiently earlier than the effective U.S. filing date and any foreign priority date so that the particular month of publication is not in issue).
Zhang et al.; Lamellar supramolecular materials based on a chelated metal complex for organic dye adsorption; RSC advances; 6(40); pp. 33295-33301; Mar. 29, 2016.
Rau et al.; U.S. Appl. No. 17/461,857 entitled "Therapeutic compositions of undecylenic acid and arginine," filed Aug. 30, 2021.
Jones et al.; Wound Dressings; BMJ; 332(7544); pp. 777-780; Mar. 30, 2006.
Kotan et al.; Screening of antibacterial activities of twenty-one oxygenated monoterpenes; Zeitschrift für Naturforschung C; Journal of Biosciences; 62(7-8); pp. 507-513; Aug. 1, 2007.
Marchese et al.; Antibacterial and antifungal activities of thymol: A brief review of the literature. Food chemistry; vol. 210; pp. 402-414; Nov. 1, 2016.
Nall et al.; Dietary supplementation of L-arginine amd conjugated linoleic acid reduces retroperitoneal fat mass and increases lean body mass in rats; The Journal of nutrition; 1397(7); pp. 1279-1285, Jul. 1, 2009.

\* cited by examiner

| Description | UCA concentration | UCA:LARG molar ratio | Result |
|---|---|---|---|
| UCA stock | 180 mg/mL | 1:1.71 | Soluble |
| UCA up 10% | 198 mg/mL | 1:1.57 | Soluble |
| UCA down 10% | 162 mg/mL | 1:1.91 | Soluble |
| UCA up 20% | 216 mg/mL | 1:1.44 | Soluble |
| UCA down 20% | 144 mg/mL | 1:2.15 | LARG insoluble |
| UCA up 30% | 234 mg/mL | 1:1.32 | UCA insoluble |
| UCA down 30% | 54 mg/mL | 1:2.47 | LARG insoluble |

FIG. 3

| UCA concentration | LARG concentration | UCA:LARG molar ratio | Result |
|---|---|---|---|
| 0 mg/mL | 177 mg/mL | - | Soluble |
| 50 mg/mL | 116 mg/mL | 1:2.12 | Soluble |
| 65 mg/mL | 108 mg/mL | 1:1.76 | Soluble |
| 75 mg/mL | 98 mg/mL | 1:1.39 | Soluble |
| 86 mg/mL | 86 mg/mL | 1:1.06 | Soluble |
| 94 mg/mL | 78 mg/mL | 1:0.88 | Soluble |
| 103 mg/mL | 69 mg/mL | 1:0.71 | Soluble |
| 105 mg/mL | 67 mg/mL | 1:0.68 | UCA insoluble |
| 110 mg/mL | 61 mg/mL | 1:0.58 | UCA insoluble |

FIG. 4

Freezer stability Study (-20 degrees Celsius for 24 hours)

| UCA concentration | LARG concentration | UCA:LARG molar ratio | Result |
|---|---|---|---|
| 84 mg/mL | 88 mg/mL | 1:1.00 | Stable |
| 94 mg/mL | 78 mg/mL | 1:0.88 | Unstable |
| 96 mg/mL | 76 mg/mL | 1:0.84 | Unstable |
| 98 mg/mL | 74 mg/mL | 1:0.8 | Stable |
| 99 mg/mL | 72 mg/mL | 1:0.77 | Unstable |
| 101 mg/mL | 70 mg/mL | 1:0.73 | Unstable |
| 103 mg/mL | 69 mg/mL | 1:0.71 | Unstable |

| | | Hydrophobic Side Chain – Aliphatic | | | | | Hydrophobic Side Chain – Aromatic | | | Polar Neutral Side Chains | | | | | Electrically Charged Side Chains – Acidic | | Electrically Charged Side Chains – Basic | | | Unique Amino Acids | | Other |
|---|---|---|---|---|---|---|---|---|---|---|---|---|---|---|---|---|---|---|---|---|---|---|
| | | Alanine | Isoleucine | Leucine | Methionine | Valine | Phenyl-alanine | Tryptophan | Tyrosine | Asparagine | Cysteine | Glutamine | Serine | Threonine | Aspartic acid | Glutamic acid | Arginine | Histidine | Lysine | Glycine | Proline | D-arginine |
| C4 | Butanoic acid / Butyric acid | | | | | | | | | | | | | | | | ? | ? | ? | | | |
| C5 | Pentanoic acid / Valeric acid | | | | | | | | | | | | | | | | ? | ? | ? | | | |
| C6 | Hexanoic acid / Caproic acid | | | | | | | | | | | | | | | | Yes | ? | Yes | No | | |
| C7 | Heptanoic acid / Enanthic acid | | | | | | | | | | | | | | | | Yes | + | + | | | |
| C8 | Octanoic acid / Caprylic acid | | | No | | | No | | | No | | | | | No | | Yes | Yes | Yes | No | | |
| C9 | Nonanoic acid / Pelargonic acid | | | | | | | | | | | | | | | | Yes | + | + | | | |
| C10 | Decanoic acid / Capric acid | No | No | No | No | No | No | | No | No | No | No | No | No | No | | Yes | Yes | Yes | No | No | No |
| C11 | Undecanoic acid / Undecylenic acid | | | | | | | | | | | | | | | | Yes | Yes | Yes | | | |
| C12 | Dodecanoic acid / Lauric acid | | | No | | | | | | | | | | | No | | Yes | Yes | Yes | No | No | |
| C13 | Tridecanoic acid / Tridecylic acid | | | | | | | | | | | | | | | | Yes | + | + | | | |
| C14 | Tetradecanoic acid / Myristic acid | | | | | | | | | | | | | | | | Yes | Yes | Yes | | | |
| C15 | Pentadecanoic acid / Pentadecylic acid | | | | | | | | | | | | | | | | + | + | + | | | |
| C16 | Hexadecanoic acid / Palmitic acid | | | | | | | | | | | | | | | | + | Yes | + | | | |
| C17 | Heptadecanoic acid / Margaric acid | | | | | | | | | | | | | | | | + | + | + | | | |
| C18 | Octadecanoic acid / Stearic acid | | | No | | | No | | No | No | | No | | | No | | + | + | + | No | No | |
| | Linoleic acid | | | | | | | | | | | | | | | | Yes | Yes | Yes | | | |
| C20 | Eicosanoic acid / Arachidic acid | | | | | | | | | | | | | | | | Yes | Yes | Yes | | | |
| | Arachidonic acid | | | | | | | | | | | | | | | | Yes | Yes | Yes | | | |

FIG. 26

GS-1-2 24hrs PC3 Human Prostate Cancer Cells

FIG. 35

THERAPEUTIC COMPOSITIONS

CROSS REFERENCE TO RELATED APPLICATIONS

This patent application is a national phase application under 35 USC 371 of International Patent No. PCT/US2019/054044, titled "THERAPEUTIC COMPOSITIONS, filed Oct. 1, 2019, now International Publication No. WO 2020/072479, which claims priority to each of: U.S. provisional patent application no. 62/739,844, titled "ANTI-PATHOGENIC THERAPEUTIC COMPOSITIONS", filed on Oct. 1, 2018; U.S. provisional patent application no. 62/845,858, titled "THERAPEUTIC COMPOSITIONS," filed on May 9, 2019; and U.S. Provisional Patent Application no. 62/845,859, titled "THERAPEUTIC COMPOSITIONS," filed on May 9, 2019. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Compositions of fatty acids (e.g., C4-C40 fatty acids, C4-C20 fatty acids, C8-C20 fatty acids) including but not limited decanoic acid, octanoic acid and undecylenic acid, etc.) and amino acids (e.g., amino acids that have electrically charged basic side chains, including but not limited to L-arginine and L-lysine) and therapeutic methods of using them, e.g., for anti-pathogen (antibacterial, anti-viral, anti-fungal, anti-microbial) and anti-cancer uses.

BACKGROUND

Pathogens, such as bacteria, viruses, or other microorganisms that can cause disease, are increasingly difficult to treat, particularly with the increasing advent of antibiotic resistant forms of pathogens. The United States Center for Disease Control (CDC) publishes a list of pathogenic threats, many of which include drug-resistant microorganisms and microorganisms for which no effective drug therapy exists. For example, bacterial infections of the skin and underlying tissue present a significant clinical treatment issue. These types of infections commonly involve gram-positive bacteria that colonize on the skin and underlying tissue and symptoms can range from mild discomfort to death. Bacteria cause a number of skin conditions such as impetigo, cellulitis, boils, and acne. Deep tissue infections of surgical wounds or traumatic wounds can invade the blood stream leading to septicemia and death.

Currently, many skin infections that are caused by gram-positive bacteria are aggressively treated with antibiotics. However, as strains of pathogenic bacteria develop antibiotic resistance mechanisms, it becomes crucial to develop novel therapies that inhibit bacterial growth without using traditional antibiotics. In recent years, the issue of bacterial antibiotic resistance has become much more recognized with the development of so-called 'superbugs' such as methicillin-resistant *Staphylococcus aureus* (MRSA) and *vancomycin-resistant enterococcus* (VRE). These bacteria are common skin pathogens that have developed significant antibiotic resistance. With the continued use of antibiotics in both humans and animals bred for consumption, many common strains of skin bacteria are developing widespread antibiotic resistance leading to a serious health care issues. Common bacteria that are implicated in skin infections are Methicillin resistant *Staphylococcus aureus, S. pyogenes* and *S. pneumoniae, E. faecalis* and *S. agalactiae*. As these bacteria colonize the skin they break down the epidermis, induce an inflammatory response, and if untreated, invade into deeper tissue causing cellulitis. In extreme cases the bacteria invade the circulatory system causing sepsis and possible death.

It has become evident to the medical community that novel treatments must be developed to address this issue. However, many pharmaceutical companies have not aggressively pursued the development of new, antimicrobial treatments for skin and wound infections.

The number of people suffering from cancer and multi-resistant infections has increased in recent years, such that both diseases are already seen as current and future major causes of death. Moreover, chronic infections are one of the main causes of cancer, due to the instability in the immune system that allows cancer cells to proliferate. Likewise, the physical debility associated with cancer or with anticancer therapy itself often paves the way for opportunistic infections. It is urgent to develop new therapeutic methods, with higher efficacy and lower side-effects. In particular, it would be beneficial to provide anti-pathogenic agents that may also have anti-cancer benefits.

Described herein are compounds and methods of using them to treat a number of pathogens, including both gram-negative and gram-positive bacteria, fungi and viruses. These compounds may also be useful to treat cancer, and methods of treating or preventing cancer are also described.

SUMMARY OF THE DISCLOSURE

The present invention relates to compositions of fatty acids and amino acids for use as a therapeutic composition. Examples of fatty acids include unsaturated fatty acids (e.g., undecylenic acid (UCA)), and saturated fatty acids (e.g. lauric acid). Examples of amino acids include aliphatic amino acids (e.g., L-arginine (LARG)), aromatic amino acids (e.g. Histidine) and imino amino acids (e.g. proline) and amino acids having electrically charged basic side chains (e.g., Arginine, Histidine, and Lysine). In some variations, the amino acids may have be Arginine (e.g., LARG) and/or Lysine. These compositions may be selected for relatively high chemical stability, particularly at lower temperatures, and relatively long shelf-life, along with high-efficacy and high-safety.

Also described herein are therapeutic methods for treating a patient with these compositions, including for use to treat a communicable disease, such as an anti-pathogenic composition and/or anti-cancer composition. Anti-pathogenic may include antimicrobial, antibacterial, antifungal, antiviral, etc. Anti-cancer may include anti-tumor, anti-proliferation, anti-neoplastic etc. These compositions may find particular use as antibacterial, antiviral and in some variations, anticancer compositions. The composition may be used for topical application. For example, in some variations, they may be applied to the skin (cutaneously) for a local (topical) or body-wide (systemic) effect, including via delivery through the skin by a patch (transdermally) for a systemic effect. In some variations, they may be applied orally, in some variations, they may be applied by injection (e.g., intravenously, intramuscularly, intrathecally, subcutaneously, etc.). In some variations, they may be applied sublingually or between the gums and cheek (e.g., buccally). In some variations, they may be applied rectally or vaginally. In some variations, they may be applied intraocularly and/or by the optic nerve. In some variations they may be sprayed into the nose and absorbed through the nasal membranes (nasally) and/or breathed into the lungs, usually through the mouth (by inhalation) or mouth and nose (by nebulization).

In general, described herein are therapeutic compositions that include a fatty acid and an amino acid, and in particular a C4-C20 fatty acid and an amino acid such as an amino acid having an electrically charged basic side chain; for example, described herein are therapeutic compositions of undecylenic acid and L-Arginine in a ratio within a working range to produce an anti-pathogenic and/or anti-cancer effect (e.g., having a molar ratio of fatty acid to amino acid of between about 1:0.6 to about 1:1.6, e.g., between about 1:0.7 to about 1:1.6). For example, described herein are therapeutic compositions comprising a mixture of undecylenic acid: L-Arginine in a ratio of between about 1:0.6 to about 1:1.6. In some variations a therapeutic composition comprises a mixture of undecylenic acid: L-Arginine in a ratio of between about 1:0.6 to about 1:1.6, wherein the therapeutic composition does not include cetyl alcohol. The compositions described herein may not include any organic solvents. In some variations, a therapeutic composition comprises a mixture of undecylenic acid: L-Arginine in a ratio of between about 1:0.6 to about 1:1, wherein the concentration of L-Arginine is between 0.01 mg/mL and 182 mg/mL.

The ratio of undecylenic acid: L-Arginine may be between 1:0.6 to about 1:1. In some variations the ratio of fatty acid to amino acid (e.g., undecylenic acid: L-Arginine) is in an approximately 1:1 molar ratio. In other variations the ratio of fatty acid to amino acid (e.g., undecylenic acid: L-Arginine) is in an approximately 5:4 molar ratio. Any of these compositions may be an aqueous composition. The pH of the composition may be, e.g., between about 6 and about 10; in some variations the pH is between about 6.9 and about 7.8.

The fatty acids and amino acids described herein may form complexes of fatty acids and amino acids. Any of the compositions of fatty acids and amino acids described herein may be referred to as compositions comprising a complex of fatty acid and amino acid (which may also be referred to as a fatty acid/amino acid complex), such as a complex to UCA and LARG, etc.).

In variations in which the amino acid is L-Arginine, the concentration of L-Arginine (LARG) may be less than the solubility limit of LARG. For example, the concentration of L-Arginine may be about 182 mg/mL or less. In any of these variations, the concentration of L-Arginine may be between about 0.01 mg/mL and about 182 mg/mL. Similarly, the composition of any other additional or alternative amino acid (e.g., Lysine, Histadine, etc.) may be less than the solubility limit of that amino acid.

In general, the composition may include an excipient, diluent, or carrier (in some variations excluding cetyl alcohol). The excipient, diluent, or carrier may be configured for topical application. In some variations, the excipient, diluent, or carrier may comprise an emulsifying agent. Any of these compositions may include a cooling or heating additive.

The composition may be configured as a liquid or emulsion in a form suitable for topical administration to a human. For example, the composition may be configured for one or more of: oral, parenteral, intraperitoneal, transmucosal, transdermal, rectal, inhalable, and topical administration. The composition may be configured for coating a medical device.

Also described herein are methods of treating a patient for one or more of: an infection (e.g., a pathogen, such as a bacteria, yeast, virus, etc.) and/or a cancer. For example, a method of treating a patient to destroy a pathogen may include: administering to said patient a therapeutically effective amount of the anti-pathogenic composition, the anti-pathogenic composition comprising a mixture of fatty acid (e.g., a C4, C5, C6, C7, C8, C9, C10, C11, C12, C13, C14, C15, C16, C17, C18, C19 or C20 fatty acid) and amino acid (e.g., L-Arginine, Lysine, Histidine, etc.), such as but not limited to undecylenic acid: L-Arginine, in a ratio of between about 1:0.6 to about 1:1.6.

In some variations a method of treating a patient to destroy a pathogen using an anti-pathogenic composition may include: administering to said patient a therapeutically effective amount of the anti-pathogenic composition, the anti-pathogenic composition comprising a mixture of fatty acid (e.g., a C4, C5, C6, C7, C8, C9, C10, C11, C12, C13, C14, C15, C16, C17 C18, C19, or C20 fatty acid) and amino acid (e.g., L-Arginine, Lysine, Histidine, etc.), such as but not limited to undecylenic acid: L-Arginine, in a ratio of between about 1:0.6 to about 1:1.6, wherein the therapeutic composition does not include cetyl alcohol.

A method of treating a patient to destroy a pathogen using an anti-pathogenic composition may include: administering to said patient a therapeutically effective amount of the anti-pathogenic composition, the anti-pathogenic composition comprising a mixture of fatty acid (e.g., a C4, C5, C6, C7, C8, C9, C10, C11, C12, C13, C14, C15, C16, C17, C18, C19 or C20 fatty acid) and amino acid (e.g., L-Arginine, Lysine, Histidine, etc.), such as but not limited to undecylenic acid: L-Arginine, in a ratio of between about 1:0.6 to about 1:1.6, wherein the concentration of amino acid (e.g., L-Arginine) is between 0.01 mg/mL and 182 mg/mL.

Also described herein are cancer treatment methods, including: administering to a patient in need thereof (e.g., a patient having cancer), a therapeutically effective amount of a composition comprising a mixture of fatty acid (e.g., a C4, C5, C6, C7, C8, C9, C10, C11, C12, C13, C14, C15, C16, C17, C18, C19 or C20 fatty acid) and amino acid (e.g., L-Arginine, Histidine, Lysine, etc.), such as but not limited to undecylenic acid: L-Arginine, in a ratio of between about 1:0.6 to about 1:1. In some variations the concentration of amino acid (e.g., L-Arginine) is between 0.01 mg/mL and 182 mg/mL.

In any of these methods and compositions, the ratio of fatty acid to amino acid may be an approximately 1:1 or 5:4 molar ratio. This ratio, of approximately 1:0.95 and 1:0.76, respectively, for UCA:LARG by weight may provide both efficacy and enhanced chemical stability, allowing the fatty acid and amino acid to remain in solution over time, in particular at low temperatures, including at −20 degrees C. for extended periods of time.

In any of these methods, the anti-pathogenic composition may be an aqueous composition. The pH of the anti-pathogenic composition may be between about 6 and about 10; for example, the pH of the anti-pathogenic composition may be between about 6.9 and about 7.8.

In any of these methods the concentration of amino acid (e.g., L-Arginine) in the composition may be 182 mg/mL or less, e.g., the concentration of amino acid (e.g., L-Arginine) may be between 0.01 mg/mL and 182 mg/mL.

Administering may comprise applying the anti-pathogenic composition to the patient's skin. In some variations, administering comprises applying the anti-pathogenic composition to the patient's wound. In some variations, administering comprises applying the anti-pathogenic composition systemically to the patient. In some variations, administering comprises spraying the anti-pathogenic composition on the patient. In some variations, administering comprises releasing the anti-pathogenic composition from a medical device. For example, administering may comprise contacting the patient with a surface of a medical device comprising the anti-pathogenic composition.

The composition (e.g., the anti-pathogenic composition, the anti-cancer composition, etc.) may further comprise an excipient, diluent, or carrier, excluding cetyl alcohol; said excipient, diluent, or carrier may be configured for topical application. The excipient, diluent, or carrier may comprise an emulsifying agent.

Any of these compositions (e.g., the anti-pathogenic composition, the anti-cancer composition, etc.) may further comprise a cooling or heating additive, and/or may be configured as a liquid or emulsion in a form suitable for topical administration to a human.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3 is a table (Table 1) showing UCA:LARG solubility with LARG above solubility limit.

FIG. 4 is a table (Table 2) showing UCA:LARG solubility with LARG below solubility limit.

FIG. 9 shows the same data as FIG. 8, but with a y-axis that extends to 1,000,000 (1.0×10$^6$) CFU/mL. FIG. 10 shows the same data on a y-axis that extends to 100,000 (1.0×10$^5$) CFU/mL. FIG. 11 shows the same data on a y-axis that extends to 30,000 (3.0×10$^4$) CFU/mL.

FIG. 18A shows treated cells at 1:64 dilution of GS-1, showing the greatest amount of cell death. FIG. 18B shows cells treated with a 1:128 dilution of GS-1. FIG. 18C shows cells treated with a 1:256 dilution of GS-1. FIG. 18D shows cells treated with a 1:512 dilution of GS-1. FIG. 18E shows the untreated control.

FIG. 26 is a table matrix showing the results of testing a variety of amino acid and fatty acid combinations. Exemplary C4-C20 fatty acids are listed in the column, while amino acids (grouped by characteristics) are shown along the top. Negative results and positive results are indicated in the corresponding boxes, where negative results indicate a failure to form a solution and/or to have significant anti-pathogenic/anti-cancer effect. Positive results indicated the that combination of amino acid and fatty acid formed a therapeutic composition, e.g., in a molar ratio of fatty acid:amino acid of between about 1:0.6 to about 1:1.6. Question marks, (−) and (+) indicate preliminary testing, while "Yes" or "No" indicated confirmed data.

FIG. 35 is a graph illustrating the in vitro anti-viral activity of an example of a therapeutic composition of fatty acid and amino acid as described herein, in which the molar ratio of fatty acid:amino acid is between about 1:0.6 and about 1:1.6 (in this example, LARG and UCA, GS-1) against pseudo-Ebola infected cells at various concentrations.

DETAILED DESCRIPTION

Figure 1:
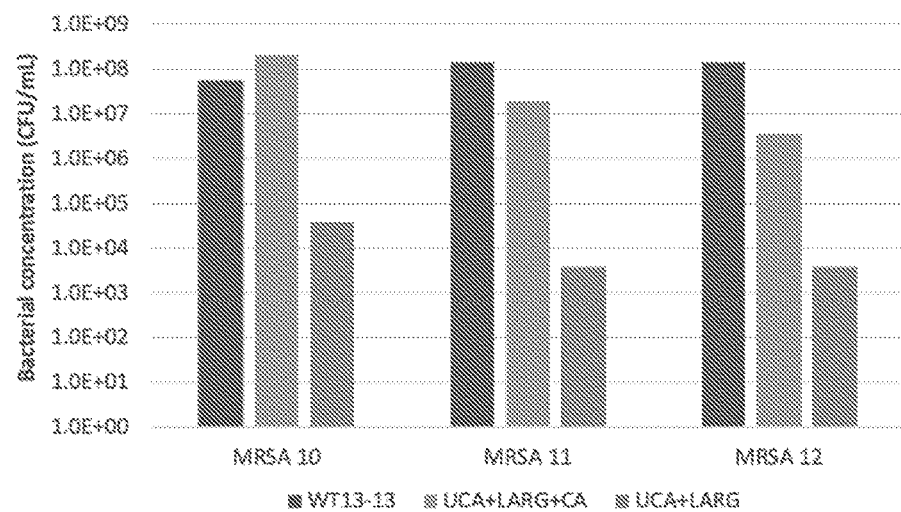
FIG. 1 is a graph showing the antibacterial effect of different compositions including LARG and UCA.

In general, described herein are therapeutic compositions (e.g., anti-pathogenic and/or anti-cancer compositions) that include both a fatty acid (e.g., one or more of a C4, C5, C6, C7, C8, C9, C10, C11, C12, C13, C14, C15, C16, C17, C18, C19, or C20 fatty acid, etc., such as one or more of undecylenic acid, decanoic acid, octanoic acid, linoleic acid, etc.) and an amino acid (e.g., one or more of: L-arginine, Lysine, Histidine, etc.) in which the ratio of the total fatty acid to the total amino acid is within a range of about 1:0.60 to about 1:1.6 (e.g., between about 1:0.6 and 1:1.2, between about 1:0.6 and 1:1.0, about 1:<1.0, etc.). The concentration of the amino acid in the composition may be less than the solubility limit of the amino acid. In some variations, the composition may include a ratio of fatty acid to amino acid (e.g., UCA:LARG ratio) that is approximately a 1:1 molar ratio (e.g., about 1:0.95 by weight). In some variations, the composition may include a ratio of fatty acid to amino acid (e.g., UCA:LARG ratio) that is approximately a 5:4 molar ratio (e.g., about 1:0.76 by weight). These compositions may have enhanced stability and efficacy, including over extended periods of time at −20° C. or less.

Compositions outside of this range are much less effective, or ineffective, and/or may be unstable. For example, PCT/US2018/018077, filed on Feb. 13, 2018 (titled "ANTI-PATHOGENIC THERAPEUTIC COMPOSITIONS"), herein incorporated by reference in its entirety and US 2015/0366925, filed on Jan. 27, 2014 (as PCT application no. PCT/US14/13120) describes antibacterial compositions of Chinese rhubarb extract, and in particular, compositions including an active ingredient of Chinese rhubarb extract, Rhein. These compositions typically included L-arginine (LARG) and undecylenic acid (UCA) as accessory molecules in compositions including other materials for treatment as an antimicrobial material; LARG and UCA were shown to have no effect on bacterial growth without the addition of Chinese rhubarb extract/Rhein (see, for example, FIGS. 4-7 of US 2015/0366925). This previous work described drug products that included a combination of L-arginine, undecylenic acid, Chinese rhubarb/Rhein, cetyl alcohol (an excipient) and water. Based on these initial filings, at least the three components, LARG, UCA and Chinese rhubarb extract/Rhein were required in order to achieve a robust therapeutic effect. This work further taught that cetyl alcohol was needed to get these components into solution together. It was therefore believed that the highest efficacy would occur at the maximum achievable concentration of all three components (individually and collectively). As a result, LARG was always included at above its solubility limit (e.g., super-saturated).

Surprisingly, the inventors have developed a composition in which just a fatty acid, such as UCA, and an amino acid, such as LARG, may together form a remarkably effective anti-pathogenic and anti-cancer composition when Chinese rhubarb extract (including Rhein) is absent from the composition. In particular, described herein are compositions of virtually any C4-C40 (e.g., C4-C20, C8-C20, C8-C18, C4-C18) fatty acid with certain amino acids (e.g., Arginine, Histidine, Lysine), including but not limited to UCA and LARG, within a defined range of concentrations that have superior stability in solution as well as efficacy as anti-pathogenic and/or anti-cancer therapies. Further, any of these compositions, including compositions of UCA and LARG, may be made without cetyl alcohol or other similar excipients, previously thought to be necessary for solubility of the fatty acid and amino acid (e.g., to keep UCA and LARG in solution together). Surprisingly, excipients such as cetyl alcohol significantly inhibit the efficacy of the fatty acid and amino acid (e.g., UCA and LARG) compositions. For example, the highest efficacy of an UCA/LARG composition occurs at concentrations of UCA and LARG that are well below the maximum achievable concentration of all three components, and in particular, occur at concentrations of LARG below its solubility limit. As described herein, compositions of fatty acids and amino acids (e.g., UCA/LARG) have significant efficacy (e.g., anti-pathogenic and/or anti-cancer efficacy) only within a specified window of UCA:LARG concentration ratios, which can only be achieved when LARG is at or below its solubility limit (and in the absence of Chinese rhubarb extract/Rhein and/or cetyl alcohol). Further, this optimal range (e.g., ratios of UCA to LARG of 1 to <1, such as between about 1:0.6 to 1:1.6, e.g., between about 1:0.6 to 1:1) is tightly circumscribed: at one end of the window (e.g., above about 1:1.6) there is sharp drop off in efficacy. At the other end of the window of optimal range there is a solubility drop off, where the fatty acid (e.g., UCA) solubility drops off very sharply. Inside the window, efficacy is far greater than previously observed, and there is a strong trend towards an optimum value.

Prior compositions of UCA and LARG for use as an antimicrobial included both Chinese rhubarb/Rhein and cetyl alcohol (CA), and the Chinese Rhubarb extract (Rhein) and cetyl alcohol were believed to be necessary. Surprisingly, the inventors have found that removing both Chinese rhubarb/Rhein and CA dramatically improved the activity of the resulting compound; this improvement was even more profound when the ratio of the UCA:LARG was adjusted to be between about 1:0.6 and 1:1.6. This was unexpected, as Rhein has antimicrobial activity and CA is a widely accepted excipient (and hence should not affect efficacy).

For example, FIG. 1 shows the antimicrobial effect of various compositions including UCA and LARG against three MRSA isolates. In FIG. 1, one exemplary composition, "WT13-13" contains UCA, LARG, Rhein, CA and water; the composition of UCA+LARG+CA contains no Rhein (with water); and the composition of UCA+LARG contains no Rhein and no CA (with water). In all cases the UCA and LARG concentrations were held constant. Note that efficacy is reported in terms of the viable bacterial concentration (in CFU/mL) remaining after 24 hours of treatment with the drug product (in compliance with CLSI guidelines). In this first example, the composition including just UCA and LARG was more strongly antimicrobial than compositions including Chinese rhubarb extract/Rhein, UCA and LARG, or even UCA and LARG with the excipient, CA. In FIG. 1, the ratio of UCA and LARG is un-optimized.

Figure 2A:
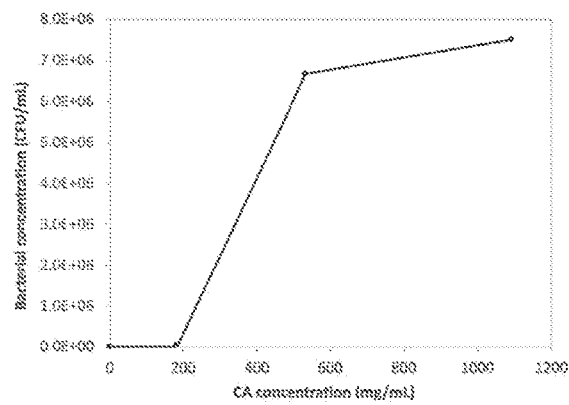
FIGS. 2A-2B are graphs showing the inhibitory effect of cetyl alcohol (CA) on the ability of compositions of LARG and UCA to prevent bacterial growth.
Figure 2B:
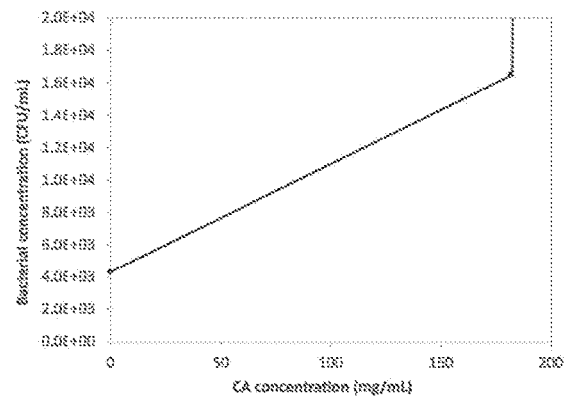

The UCA+LARG and excipient (e.g., CA) compound was further tested by varying the concentration of CA and testing antimicrobial efficacy. FIGS. 2A-2B show the resulting efficacy (average taken across three MRSA isolates). FIG. 2A shows a full scale on the y-axis (e.g., up to $8 \times 10^6$ CFU/mL), and FIG. 2B shows a zoomed-in y-axis that better illustrates the low CA concentration behavior. Efficacy is reported in terms of the viable bacterial concentration (in CFU/mL) remaining after 24 hours of treatment. As shown, increasing amounts of CA in the UCA and LARG composition resulted in a decrease in efficacy.

Thus, removing Chinese rhubarb/Rhein and CA resulted in better efficacy. Furthermore, CA imparted a clear inhibitory effect as a function of its concentration. These findings conflict with the previously published data showing that UCA and LARG alone (or in combination) did not show significant anti-microbial (e.g., antibacterial) effect. See, e.g., FIGS. 4-7 of US 2015/0366925.

In particular, previously described compositions of UCA and LARG included tightly controlled UCA and LARG concentrations. For example, at full strength, the concentration of LARG was 293 mg/mL and UCA was 180 mg/mL, resulting in a UCA:LARG ratio of 1:1.62. That solubility limit of LARG is 182 mg/mL. The higher ratio of LARG to UCA in these compositions with Chinese rhubarb extract/Rhein was believed to enhance the efficacy of the Chinese Rhubarb, including assisting in maintaining the extract/Rhein in solution.

Initial experiments began by varying the ratio of LARG and UCA. For example, as shown in FIG. 3 (Table 1), LARG was held at 293 mg/mL, and the concentration of UCA was varied up and down in increments of 10%. FIG. 3 summarizes the effect of these changes on the solubility of UCA and/or LARG, showing that the UCA:LARG ratio needs to be tightly controlled to achieve solubility of both ingredients.

It was previously believed that LARG should be maintained in excess, and in particular, at concentrations above its solubility (e.g., supersaturated, such as at 293 mg/mL) in order to maintain the activity and/or solubility of the presumed active ingredient, Chinese Rhubarb extract/Rhein. However, as described herein, reducing the LARG concentration below its solubility limit resulted in a much wider range of UCA:LARG ratios that can be achieved and, in particular, including, e.g., ratios of 1:1 and below (i.e. where there is more UCA than LARG by weight), lower ratios have a higher therapeutic efficacy without the use of Chinese Rhubarb extract/Rhein. For example, FIG. 4 (showing table 2) summarizes the solubility results, showing compositions in which LARG concentration was below the solubility limit of LARG (e.g., 182 mg/mL), and various ratios of UCA:LARG were examined It is evident from FIG. 4 that there exists a solubility "ledge", whereby UCA becomes insoluble between UCA:LARG ratios of 1:0.67 and 1:0.64. A very tight range was observed. The actual concentrations of UCA and LARG differ by 2 mg/mL (e.g., 1.9% and 2.9%, respectively) between these two points.

Figure 5:
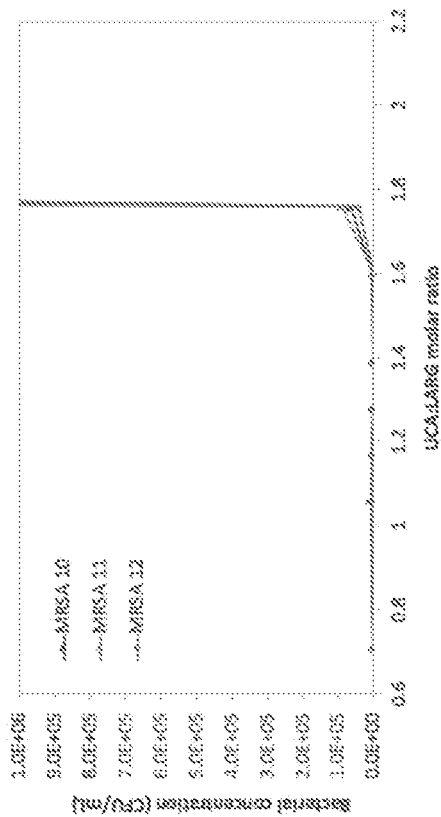
FIG. 5 is a graph showing the bactericidal effect of various ratios of UCA:LARG on three MRSA isolates.
Figure 6:
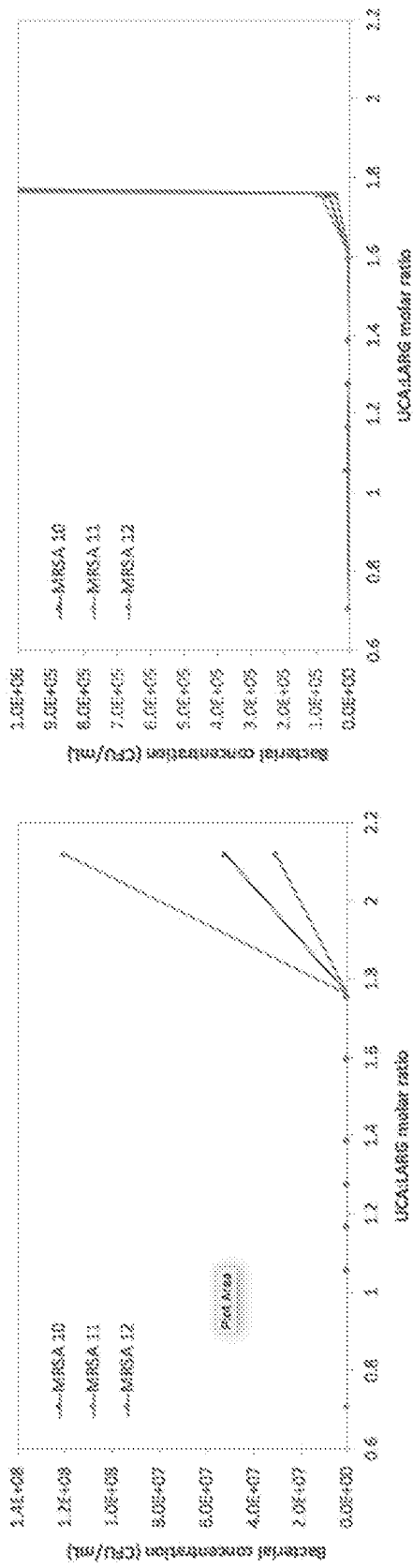
FIG. 6 is a graph showing the bactericidal effect of various ratios of UCA:LARG on three MRSA isolates at a finer scale than FIG. 5.
Figure 7:
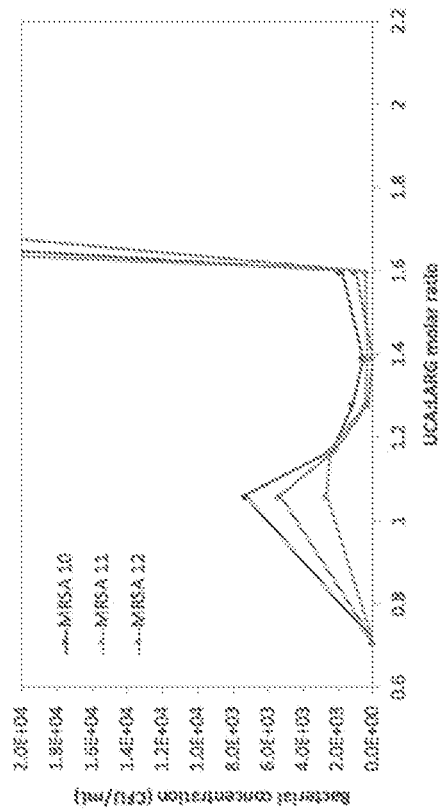
FIG. 7 is a graph showing the bactericidal effect of various ratios of UCA:LARG on three MRSA isolates at a finer scale than FIGS. 5 and 6.

Thus, while it is possible to formulate a wider range of UCA:LARG concentrations with LARG below its solubility limit (as opposed to when it is above its limit), only a subset of these ratios has therapeutic efficacy. A number of UCA:LARG ratios were tested across the full solubility range (e.g., between 1:2.00 and 1:0.67) against bacteria. In all cases, the drug products comprised UCA, LARG and sterile water (both Rhein and CA were excluded), and the total percentage of active ingredients was held constant at 17% by adjusting the water content. FIGS. 5-7 and 8-11 summarize the results of these efficacy tests. For example, FIG. 5 shows an example of compositions of UCA and LARG (without Rhein or CA) applied at different ratios of UCA:LARG, showing a dramatic antimicrobial effect at ratios of about 1:1.6 (e.g., about 1:<1.5). In FIG. 5, the y-axis shows the full scale (up to $1.5 \times 10^8$ CFU/mL), while FIGS. 6 and 7 provide zoomed y-axes to better show the change in efficacy that is strongly dependent on the ratio of UCA:LARG. Note that efficacy is reported in terms of the viable bacterial concentration (in CFU/mL) remaining after 24 hours of treatment with the drug product (in compliance with CLSI guidelines). Drug dilution in these examples was 1:16 from 17% active throughout in FIG. 5, FIG. 6, and FIG. 7.

As mentioned, previously described drug products contained LARG above its solubility limit and, as such, carried greater than 1:1 UCA:LARG ratios (e.g., typically greater than 1:1.6). For example, the previously described compound including Rhein, WT13, had a UCA:LARG ratio of 1:1.62, which is outside of the effective therapeutic range (e.g., within the "ledge" region in which therapeutic activity falls off dramatically). Dropping the UCA:LARG ratio down dramatically improved the efficacy. For example, a UCA:LARG ratio of 1:0.67 is over 50,000× more efficacious than a ratio of 1:1.62 (which is the ratio used in the previously described drug product with LARG super-saturated).

Figure 8:
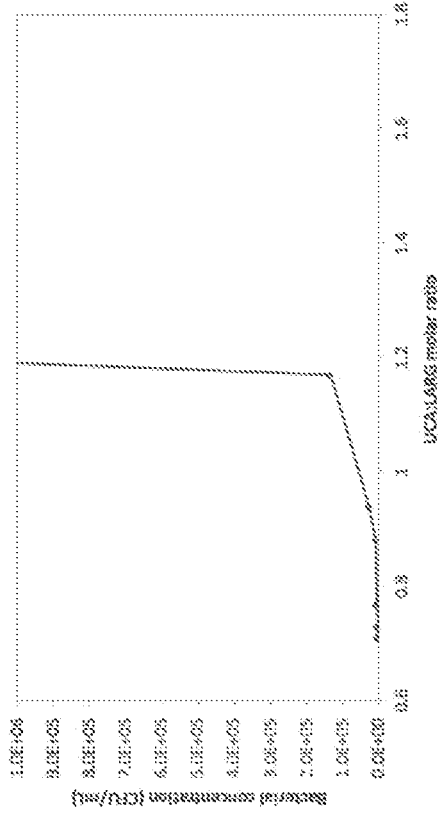
FIGS. 8-11 show the average bacterial concentration taken from three MRSA isolates (MRSA 10, 11 and 12) as a function of the UCA:LARG ratio. The y-axis (bacterial concentration, in CFU/mL) in FIG. 8 extends, logarithmically, to a concentration of 140,000,000 (1.4×10$^8$) CFU/mL.
Figure 9:
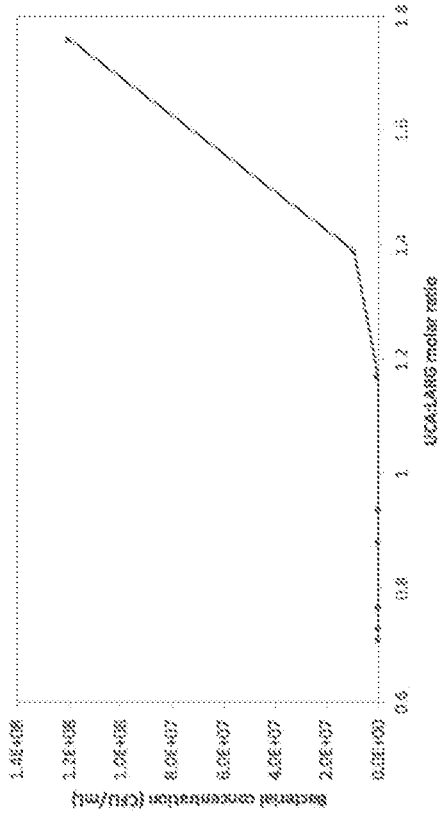
Figure 10:
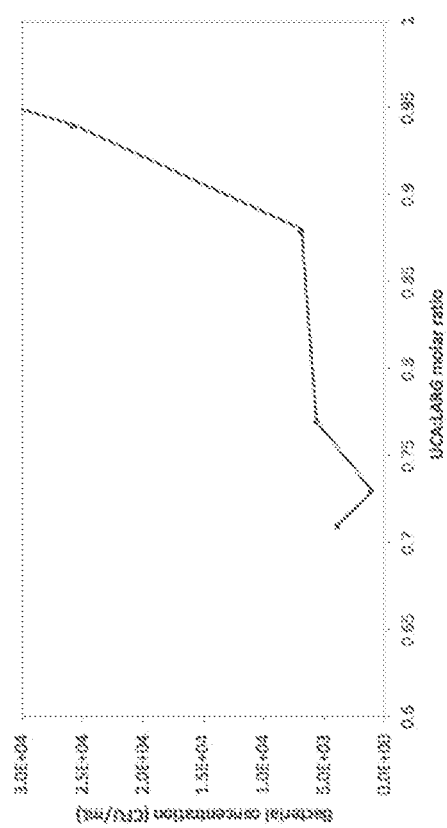
Figure 11:
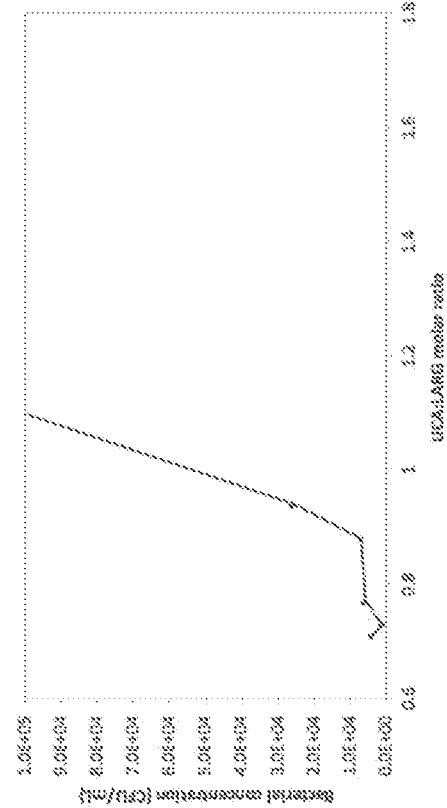

To further investigate the efficacy behavior at UCA:LARG ratios below about 1:1 (where the above graphs have bacterial concentrations of zero), the above experiments were repeated with a higher drug dilution of 1:64 from 17% active. FIGS. 8-11 show the average bacterial concentration taken from three MRSA isolates (MRSA 10, 11 and 12) as a function of the UCA:LARG ratio. FIG. 8 shows a full scale on horizontal and vertical axes, while FIG. 9 and FIG. 10 show zoomed vertical axes, and FIG. 11 provides zoomed vertical and horizontal axes. Based on this data, a UCA:LARG ratio of about 1:1 or less (e.g., 1:≤1) is superior to greater than 1:1 (e.g., 1:>1). As described in greater detail herein, an optimum activity window of UCA:LARG ratios may be present, e.g., generally ratios in which for every mass unit of UCA, there is 1.5 mass units or less of LARG. More particularly, for every mass unit of UCA, there is 1.4 mass units or less of LARG, 1.3 mass units or less of LARG, 1.2 mass units or less of LARG, 1.1 mass units or less of LARG, 1.0 mass units or less of LARG, etc. For example, the range of ratios of UCA:LARG may be between about 0.65 mass units of LARG and about 1.5 mass units of LARG per mass unit of UCA (e.g., UCA:LARG ratio of between 1:0.6 and 1:1.6).

Figure 12:
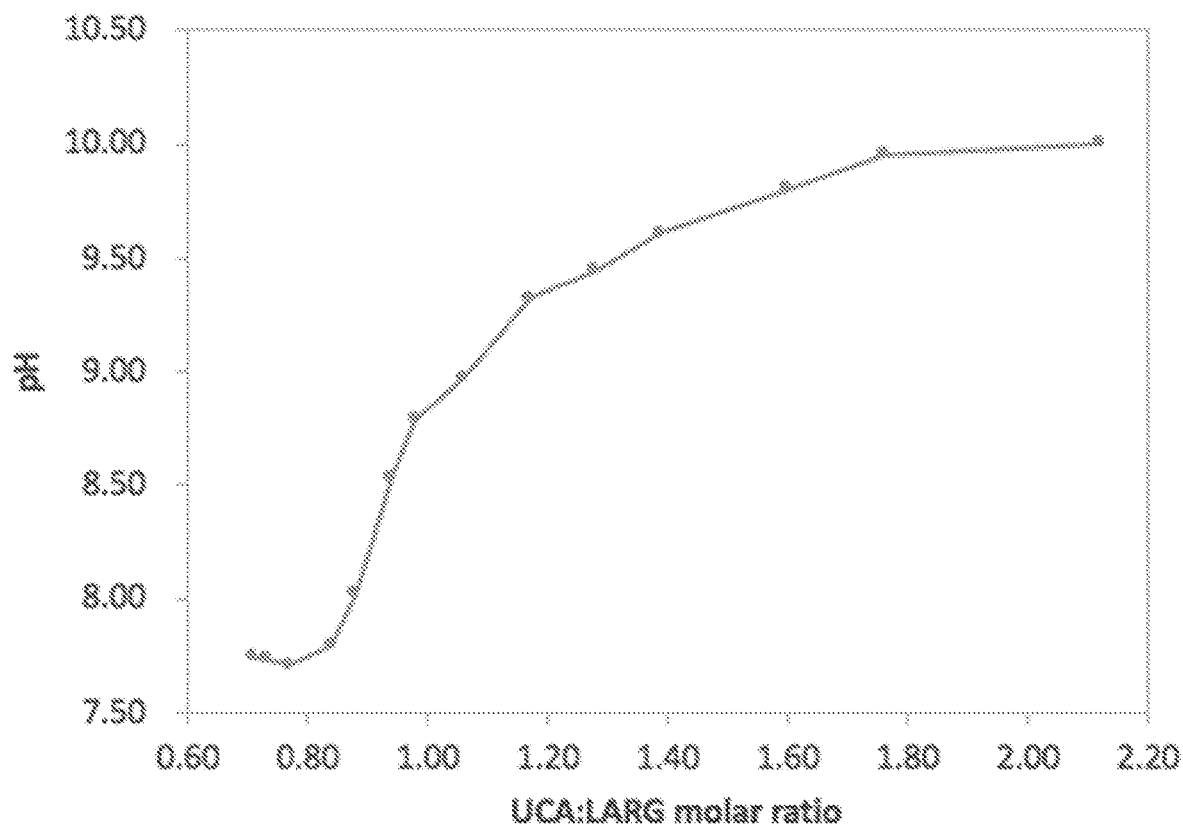
FIG. 12 is a graph showing the pH of various compositions including different UCA:LARG ratios in water.

In further support of this optimum window, pH tests were performed on various compounds of UCA:LARG and a correlation that indicates an optimum concentration relationship between UCA and LARG was identified. FIG. 12 shows the pH as a function of the UCA:LARG ratio. In this example, at ratios above about 1:0.80 the pH rises sharply, which may be due to a relative abundance of LARG as compared to UCA (LARG is highly basic). High pH in a drug composition may present a risk of skin irritation in some patients, and can also be difficult for the body to buffer for systemic applications. The more neutral pH of the optimum ratio (e.g., 1:1.0 or less, e.g., 1:<1) may be desirable.

At the previously described UCA:LARG ratio of 1:1.62, cetyl alcohol (CA) and Rhein were able to be placed into solution readily, and often off-gassing of ammonia (released from LARG) was detected. In contrast, at the optimized ratio range (e.g., between 1:0.6 and 1:1.6, e.g., between about 1:0.7 and 1:1.6) neither CA nor any Rhein may be readily put or maintained in solution (and ammonia off-gassing has not been detected).

Thus, described herein are pharmaceutically effective compositions having a range of UCA:LARG molar ratios within an effective range of between about 1:0.6 to about 1:1.6. The lower end (e.g., 1:0.6) may be lower, e.g., 1:<0.65, if, for example, UCA is made soluble. These compositions may explicitly exclude CA, however any other excipient or buffer may be used. The range may be, for example, between about 1:0.6 (or about 1:0.65, about 1:0.66, about 1:0.67, about 1:0.68, about 1:0.69, about 1:0.7, about 1:0.72, etc.) to about 1:1.6 (e.g., about 1:1.55, about 1:1.5, about 1:1.45, about 1:1.4, about 1:1.35, about 1:1.30, about 1:1.25, about 1:1.20, about 1:1.15, about 1:1.10 about 1:1.05, about 1:1.0, about 1:0.9, etc.), including any sub-ranges therein.

Also described herein are compositions of UCA and LARG substitutes (by other, similar chemicals in their respective families).

For example, described herein are compositions of fatty acids and amino acids within a range of molar ratios of about 1:0.6 and 1:1.6, e.g., fatty acid : amino acid ratios of between 1:0.6 and 1:1.6 (e.g., between about 1:0.7 to about 1:1.6, in some variations, having a molar ratio of fatty acid to amino acid of about 1:1 or about 5:4). In general, the fatty acid may be an unsaturated fatty acid (such as, but not limited to, UCA and linoleic acid, etc.) or a saturated fatty acid (such as, but not limited to, lauric acid, octanoic acid, decanoic acid, etc.). The amino acid may be an amino acid having an electrically charged basic side chain (such as, but not limited to, LARG, Lysine, etc.), or an aromatic amino acid (such as, but not limited to, Histidine), or an imino amino acid (such as, but not limited to, proline). Surprisingly, outside of these defined molar ranges the anti-pathogenic activity is significantly lost. The range may be, for example, between about 1:0.6 (or about 1:0.62, about 1:0.63, about 1:0.64, about 1:0.65, about 1:0.66, about 1:0.67, about 1:0.68, about 1:0.69, about 1:0.7, about 1:0.72, etc.) to about 1:1.5 (or about 1:1.45, about 1:1.4, about 1:1.35, about 1:1.30, about 1:1.25, about 1:1.20, about 1:1.15, about 1:1.10 about 1:1.05, etc.), including any sub-ranges therein.

The compositions described herein may include one or more other APIs or excipients. These compositions may be used across a wide range of applications/purposes including anti-bacterial, anti-viral, anti-fungal, anti-cancer, with a wide range of delivery routes including skin, systemic, oral, inhaled, intravenous and intramuscular. In particular, the compositions described herein show potent efficacy against both gram-positive and gram-negative bacteria. The anti-pathogenic compounds described herein (which may also be referred to herein as anti-pathogenic agents) are effective against a broad variety of pathogens including in particular gram-negative and gram-positive bacteria, fungi and viruses. These compositions may also be effective against other classes of bacteria, including mycobacterium, as well as against fungi.

These anti-pathogenic compounds may be used to treat or prevent infections, including bacterial infections, in, e.g., a human or non-human patient. These anti-pathogenic compounds may be used to kill, stop or slow the progression of a pathogenic infection (or to kill and/or slow or stop the growth of a pathogen in or on a body or material, such as a surface). For example, described herein are bacteriostatic compositions. For example, described herein are bacteriostatic compositions that include a mixture of between 1:0.6 to 1:1.6 fatty acid: amino acid (e.g., UCA:LARG); additional materials (excipient, diluent, or carrier) may be combined with the mixture to form the anti-pathogenic compound. In some variations, the amino acid includes L-arginine, the fatty acid includes undecylenic acid.

Any of the therapeutic (e.g., anti-pathogenic, anti-cancer) compositions described herein may be used to treat a patient, e.g., a human or non-human patient, suffering from or at risk of developing an infection and/or cancer by administering a therapeutically effective amount of one or more of the therapeutic compositions described herein including one or more amino acids and one or more fatty acids in the recited range. For example, described herein are methods of treating a patient, e.g., a human or non-human patient, suffering from or at risk of developing an infection by administering a therapeutically effective amount of a composition that contains one or more fatty acids and one or more amino acids in a molar ratio of between about 1:0.6 to 1:1.6. The range may be, for example, between about 1:0.6 (or about 1:0.66, about 1:0.67, about 1:0.68, about 1:0.69, about 1:0.7, about 1:0.72, etc.) to about 1:1.45 (or about 1:1.4, about 1:1.35, about 1:1.30, about 1:1.25, about 1:1.20, about 1:1.15, about 1:1.10 about 1:1.05, about 1:1, about 1:9, etc.), including any sub-ranges therein.

Any of the anti-pathogenic compositions described herein may be part of a kit that includes one or more of the anti-pathogenic compositions along with instructions for administration to a patient.

The one or more amino acids may include, e.g., one or more of: arginine, asparagine, aspartate, glutamate, glutamine, histidine, serine, threonine and lysine. The one or more amino acids may include, e.g., an aliphatic amino acid, including one or more of: Alanine, Arginine, Asparagine, Aspartic acid, Cysteine, Glutamine, Glutamic acid, Glycine, Isoleucine, Lysine, Leucine, Methionine, Serine, Threonine, and Valine. In particular, the one or more amino acids may include Arginine, Histidine and/or Lysine. Fatty acids may be saturated or unsaturated (e.g. mono-unsaturated or poly-unsaturated). In particular, the fatty acid may be a fatty acid having a lipid number (e.g., number of carbons) of between C4 and C20, or C4 and C18 (e.g., one or more of: Butanoic acid, Isobutyrate, Pentanoic acid, 3-Methylbutanoate, Hexanoic acid, Heptanoic acid, Octanoic acid, Nonanoic acid, Decanoic acid, Undecanoic acid, Dodecanoic acid, Tridecanoic acid, Tetradecanoic acid, (9Z)-hexadecenoic acid, Hexadecanoic acid, Heptadecanoic acid, Octadecanoic acid, (9Z,12Z)-octadeca-9,12-dienoic acid, (9Z,12Z,15Z)-octadeca-9,12,15-trienoic acid, (6Z,9Z,12Z)-octadeca-6,9, 12-trienoic acid, (5E,9E,12E)-octadeca-5,9,12-trienoic acid, (6Z,9Z,12Z,15Z)-octadeca-6,9,12,15-tetraenoic acid, (Z)-octadec-9-enoic acid, (11E)-octadec-11-enoic acid, (E)-octadec-9-enoic acid, etc.). In some variations, the fatty acid may be an unbranched fatty acid between C4 and C18 (e.g., Butanoic acid, Pentanoic acid, Hexanoic acid, Heptanoic acid, Octanoic acid, Nonanoic acid, Decanoic acid, Undecanoic acid, Dodecanoic acid, etc.). For example, an unsaturated fatty acid can be, e.g., undecylenic acid (e.g., undecanoic acid). In some variations, the fatty acid may include one or more of a C4 to C12 fatty acid (e.g., Butanoic acid, Isobutyrate, Pentanoic acid, 3-Methylbutanoate, Hexanoic acid, Heptanoic acid, Octanoic acid, Nonanoic acid, Decanoic acid, Undecanoic acid, Dodecanoic acid) or one or more of unbranched C4 to C12 fatty acid (e.g., Butanoic acid, Pentanoic acid, Hexanoic acid, Heptanoic acid, Octanoic acid, Nonanoic acid, Decanoic acid, Undecanoic acid, Dodecanoic acid), or C8 to C20 or C8 to C18.

Any of these compositions may include a cooling or heating additive, such as menthol. The compositions may contain a pharmaceutically acceptable excipient, diluent, or carrier in addition to the mixture. The amount of excipient, diluent, or carrier does not change the relative ratios (percentages) of the amino acids and fatty acids.

In some variations, a topical formulation does not include any additional excipient such as an emulsifying agent. In some variations, the excipient, diluent, or carrier may be configured for topical application. For example, the excipient, diluent, or carrier may comprise an emulsifying agent. In general, an excipient, diluent or carrier (including water) is an inactive substance that serves as the vehicle or medium for a drug or other active substance. Excipients may include bulking agents, fillers or the like. The excipient may aid in the handling of the mixture of active substances by facilitating powder flowability or non-stick properties, aiding in vitro stability (e.g., prevention of denaturation or aggregation over the expected shelf life), enhancing solubility, improving absorption and/or uptake, providing better aesthetic and/or cosmetic features, altering physical properties etc.

Examples of excipients may include: antiadherents (e.g., magnesium stearate, etc.); binders (e.g., saccharides and their derivatives: disaccharides, sucrose, lactose; polysaccharides and their derivatives: starches, cellulose or modified cellulose such as microcrystalline cellulose and cellulose derivatives including cellulose ethers such as hydroxypropyl cellulose; sugar alcohols such as xylitol, sorbitol or mannitol; protein: gelatin; synthetic polymers: polyvinylpyrrolidone or PVP, polyethylene glycol or PEG, polyvinylpyrrolidone, starch, sucrose and polyethylene glycol, methyl cellulose); coatings (e.g., cellulose ether hydroxypropyl methylcellulose, synthetic polymers, shellac, corn protein zein or other polysaccharides, gelatin); enterics (fatty acids, waxes, shellac, plastics, and plant fibers); colors (titanium oxide, azo dyes, etc.); disintegrants (e.g., cross-linked polymers: crosslinked polyvinylpyrrolidone such as crospovidone, crosslinked sodium carboxymethyl cellulose or croscarmellose sodium, glycolate, etc.); flavors (fruit extract, etc.); glidants (e.g., fumed silica, talc, and magnesium carbonate, etc.); lubricants (e.g., talc or silica, and fats, e.g. vegetable stearin, magnesium stearate or stearic acid, etc.); preservatives (e.g., antioxidants like vitamin A, vitamin E, vitamin C, retinyl palmitate, and selenium; cysteine, methionine; citric acid, sodium citrate; parabens: methyl paraben and propyl paraben); sorbents; sweeteners (e.g., sugar); vehicles (petrolatum, dimethyl sulfoxide, mineral oil, etc.); emollient/stiffening agents (Carnauba wax, Cetyl alcohol, Cetyl ester wax, Emulsifying wax, Hydrous lanolin, Lanolin, Lanolin alcohols, Microcrystalline wax, Paraffin, Petrolatum, Polyethylene glycol, Stearic acid, Stearyl alcohol, White wax, Yellow wax, etc.); emulsifier/emulsifying agent/solubilizing agent (Polysorbate 20, Polysorbate 80, Polysorbate 60, Poloxamer, Emulsifying wax, Sorbitan monostearate, Sorbitan monooleate, Sodium lauryl sulfate, Propylene glycol monostearate, Diethylene glycol monoethyl ether, Docusate sodium, etc.); humectant (e.g., Glycerin, Propylene glycol, Polyethylene glycol, Sorbitol solution, 1,2,6 Hexanetriol, etc.); thickening/gelling agent (Carbomer, Methyl cellulose, Sodium carboxyl methyl cellulose, Carrageenan, Colloidal silicon dioxide, Guar gum, Hydroxypropyl cellulose, Hydroxypropyl methyl cellulose, Gelatin, Polyethylene oxide, Alginic acid, Sodium alginate, Fumed silica, etc.); preservative (Benzoic acid, Propyl paraben, Methyl paraben, Imidurea, Sorbic acid, Potassium sorbate, Benzalkonium chloride, Phenyl mercuric acetate, Chlorobutanol, Phenoxyethanol, etc.); permeation enhancer (Propylene glycol, Ethanol, Isopropyl Alcohol, Oleic acid, Polyethylene glycol, etc.); chelating agent (Ethylene diamine tetraacetate, etc.); acidifying/alkalizing/buffering agent (Citric acid, Phosphoric acid, Sodium hydroxide, Monobasic sodium Phosphate, Trolamine, etc.); vehicle/solvent (Purified water, Hexylene glycol, Propylene glycol, Oleyl alcohol, Propylene carbonate, Mineral oil, etc.). These examples may be redundant, and different excipients may be used for different reasons, and may have dual or multiple functionalities.

The composition may be configured as a liquid or emulsion in a form suitable for topical administration to a human, including a spray, lotion, cream, ointment, tincture, etc.

Also described herein are methods of treating a patient to destroy a pathogen using an anti-pathogenic agent effective against gram-negative and gram-positive bacteria, viruses and fungi. For example, the method may include: administering to said patient a therapeutically effective amount of the anti-pathogenic agent, the anti-pathogenic agent comprising a mixture of fatty acid and amino acid as described herein, in which the molar ratio of fatty acid:amino acid is between about 1:0.6 and about 1:1.6, and any subrange thereof.

Administering may comprise applying the anti-pathogen agent to the patient's skin, to the patient's wound, etc. For example, administering may comprise spraying the anti-pathogen agent on the patient. Alternatively or additionally, administering may comprise applying the anti-pathogenic agent systemically to the patient. The compositions described herein may also be used as a coating (e.g., to a medical device, implant, etc.).

These compositions and methods of using them may be used against a variety of pathogens and/or cancers. For example, the compositions and methods of using them may be used to treat one or more of: a gram-negative bacteria, a gram-positive bacteria, a fungus, a Mycobacteria, a pneumoniae bacteria, an *E. coli* bacteria, and/or a virus. This list is exemplary only, and not intended to be exhaustive. Examples of viruses may include: smallpox virus (*Variola major* and *Variola minor*), influenza virus (type A, type B, type C, and type D), rubeola virus, mumps virus, rubella virus, varicella zoster virus, hepatitis A virus, hepatitis B virus, Herpes simplex virus 1 and 2, poliovirus, Rabies lyssavirus, Ebola virus, hantaviruses, human immunodeficiency virus (HIV), Severe acute respiratory syndrome (SARS) coronavirus, dengue virus, Zika virus, and Epstein-Barr virus.

As mentioned, these compositions may be used to cancer. For example, the compositions described herein may be used to treat: Adenoid Cystic Carcinoma, Adrenal Gland Cancer, Amyloidosis, Anal Cancer, Ataxia-Telangiectasia, Atypical Mole Syndrome, Basal Cell Carcinoma, Bile Duct Cancer, Birt Hogg Dube Syndrome, Bladder Cancer, Bone Cancer, Brain Tumor, Breast Cancer, Carcinoid Tumor, Cervical Cancer, Colorectal Cancer, Ductal Carcinoma, Endometrial Cancer, Esophageal Cancer, Gastric Cancer, Gastrontestinal Stromal Tumor—GIST, HER2-Positive Breast Cancer, Islet Cell Tumor, Juvenile Polyposis Syndrome, Kidney Cancer, Laryngeal Cancer, Leukemia, Acute Lymphoblastic Leukemia, Acute Lymphocytic (ALL) Leukemia, Acute Myeloid AML Leukemia, Chronic Lymphocytic Leukemia, Chronic Myeloid Leukemia, Liver Cancer, Lobular Carcinoma, Lung Cancer, Hodgkin's Lymphoma, Non-Hodgkin's Lymphoma, Malignant Glioma, Melanoma, Meningioma, Multiple Myeloma, Myelodysplastic Syndrome (MDS), Nasopharyngeal Cancer, Neuroendocrine Tumor, Oral Cancer, Osteosarcoma, Ovarian Cancer, Pancreatic Cancer, Pancreatic Neuroendocrine Tumors, Parathyroid Cancer, Penile Cancer, Peritoneal Cancer, Peutz-Jeghers Syndrome, Pituitary Gland Tumor, Polycythemia Vera, Prostate Cancer, Renal Cell Carcinoma, Retinoblastoma, Salivary Gland Cancer, Sarcoma, Skin Cancer, Small Intestine Cancer, Stomach Cancer, Testicular Cancer, Thymoma, Thyroid Cancer, Uterine (Endometrial) Cancer, Vaginal Cancer, and/or Wilms' Tumor. Treatment of cancer may include killing or destroying cancer cells, reducing cancer proliferation, reducing tumor size, etc.

The therapeutic agents (compositions) described herein may include an excipient, diluent, or carrier, typically excluding cetyl alcohol. Thus, described herein are anti-pathogenic (e.g., antibacterial and/or antiviral and/or anti-fungal and/or antimicrobial) compounds and methods of using them. The compounds and methods of making and using them described herein are based, in part, on the discovery of mixtures of one or more amino acids and one or more fatty acids (e.g., C4-C18) to form a mixture having specific ranges of ratios or percentages of each component of the mixture. When the components are within the desired ranges in the mixture, the composition exhibits broad anti-pathogenic therapeutic properties spanning both gram-positive (including acid fast gram-positive bacteria, such as mycobacteria) and gram-negative bacteria, as well as certain pathogenic fungi and viruses. Surprisingly, outside of these defined ranges the anti-pathogenic activity is significantly lost, particularly with respect to certain categories of pathogens, including in particular gram-negative bacteria.

These compositions may be used to directly treat a patient (e.g., human or non-human animals) exposed or potentially exposed to a pathogen, to sanitize surfaces, including medical surfaces, as a coating for a medical device or implant, or in any other use in which an anti-pathogenic material would be useful. The compositions described herein also appear to have little direct negative effect on patients (e.g., toxicity).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise. The definitions for amino acids may be as described by the National Center for Biotechnology Information, NCBI.

As used herein, the terms below have the meanings indicated.

The term "acyl" as used herein, alone or in combination, refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(O)CH3 group.

An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl" as used herein, alone or in combination, refers to a straight-chain or branched-chain hydrocarbon radical having one or more double bonds optionally substituted and containing from 2 to 20, preferably 2 to 6, carbon atoms. Alkenyl refers to a carbon-carbon double bond system attached at two or more positions such as ethenylene [(—CH=CH—),(—C::C—)]. Examples of alkenyl radicals include ethenyl, propenyl, 2-methylpropenyl, 1,4-butadienyl and the like.

The term "alkoxy" as used herein, alone or in combination, refers to an alkyl ether radical, optionally substituted wherein the term alkyl is as defined below. Examples of alkyl ether radicals include methoxy, ethoxy, n-propoxy, isopropoxy, n-butoxy, iso-butoxy, sec-butoxy, tert-butoxy, and the like.

The term "alkyl" as used herein, alone or in combination, refers to a straight-chain or branched-chain alkyl radical optionally substituted containing from 1 to 20 and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like.

The term "alkylamino" as used herein, alone or in combination, refers to an alkyl group optionally substituted attached to the parent molecular moiety through an amino group. Alkylamino groups may be mono- or dialkylated, forming groups such as, for example, N-methylamino, N-ethylamino, N,N-dimethylamino, N,N-ethylmethylamino and the like.

The term "alkylthio" as used herein, alone or in combination, refers to an alkyl thioether (R—S—) radical wherein the term alkyl is as defined above and wherein the sulfur may be singly or doubly oxidized. Examples of alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl" as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynyl" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The term "amido" as used herein, alone or in combination, refer to an amino group as described below attached to the parent molecular moiety through a carbonyl group, or vice versa.

The term "amino" as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl" as used herein, alone or in combination, means a carbocyclic aromatic system containing one, two or three rings wherein such rings may be attached together in a pendent manner or may be fused optionally substituted with at least one halogen, an alkyl containing from 1 to 3 carbon atoms, an alkoxyl, an aryl radical, a nitro function, a polyether radical, a heteroaryl radical, a benzoyl radical, an alkyl ester group, a carboxylic acid, a hydroxyl optionally protected with an acetyl or benzoyl group, or an amino function optionally protected with an acetyl or benzoyl group or optionally substituted with at least one alkyl containing from 1 to 12 carbon atoms.

The terms "arylalkyl" or "aralkyl" as used herein, alone or in combination, refers to an aryl group attached to the parent molecular moiety through an alkyl group.

The term "aryloxy" as used herein, alone or in combination, refers to an aryl group attached to the parent molecular moiety through an oxygen atom.

The term "polyether radical" means a polyether radical containing from 2 to 6 carbon atoms interrupted with at least one oxygen atom, such as methoxymethyl, ethoxymethyl or methoxyethoxymethyl radicals or methoxyethyl.

The terms "benzo" and "benz" as used herein, alone or in combination, refer to the divalent radical C6H4= derived from benzene. Examples include benzothiophene and benzimidazole.

The terms "carbamate" and "carbamoyl" as used herein, alone or in combination, refers to an ester of carbamic acid (—NHCOO—) which may be attached to the parent molecular moiety from either the nitrogen or acid end, and which may be optionally substituted as defined herein.

The term "carbonyl" as used herein, when alone includes formyl [—C(O)H] and in combination is a —C(O)— group.

The term "carboxy" as used herein, refers to —C(O)OH or the corresponding "carboxylate" anion, such as is in a carboxylic acid salt. An "O carboxy" group refers to a RC(O)O— group, where R is as defined herein. A "C carboxy" group refers to a —C(O)OR groups where R is as defined herein.

The term "chemical stability" according to the invention means that the content exhibits very little variation with respect to the initial content, namely, that the variation in content of active principle at the time T should not be less than 90% to more particularly than 95% of the initial content at T0.

The term "cyano" as used herein, alone or in combination, refers to —CN.

The term "cycloalkyl" or, alternatively, "carbocycle", as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo-fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester" as used herein, alone or in combination, refers to a carboxy group bridging two moieties linked at carbon atoms.

The term "ether" as used herein, alone or in combination, refers to an oxygen atom bridging two moieties linked at carbon atoms.

The terms "halo" or "halogen" as used herein, alone or in combination, refers to fluorine, chlorine, bromine, or iodine.

The term "haloalkyl" as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CHF—), difluoromethylene (—CF2—), chloromethylene (—CHCl—) and the like.

The term "heteroalkyl" as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2—NH—OCH3.

The term "heteroaryl" as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groupsincludecarbazolyl, benzidolyl, phenanthrolinyl, dibenzofuranyl, acridinyl, phenanthridinyl, xanthenyl and the like.

The terms "heterocycloalkyl" and, interchangeably, "heterocyclyl", as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocyclyl" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocyclyl groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocyclyl groups may be optionally substituted unless specifically prohibited.

The term "hydroxyl" as used herein, alone or in combination, refers to —OH.

The phrase "in the main chain" refers to the longest contiguous or adjacent chain of carbon atoms starting at the point of attachment of a group to the compounds of this invention.

The phrase "linear chain of atoms" refers to the longest straight chain of atoms independently selected from carbon, nitrogen, oxygen and sulfur.

The term "lower" as used herein, alone or in combination, means containing from 1 to and including 6 carbon atoms.

The term "negatively-charged ion" as used herein, refers to any negatively-charged ion or molecule, either inorganic (e.g., Cl–, Br–, I–) or organic (e.g., TsO– (i.e., tosylate)).

The term "nitro" as used herein, alone or in combination, refers to —NO2.

The term "perhaloalkyl" as used herein, alone or in combination, refers to an alkyl group where all of the hydrogen atoms are replaced by halogen atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amino group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstitutedsilyl, N3, SH, SCH3, C(O)CH3, CO2CH3, CO2H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH2CH3), fully substituted (e.g., —CF2CF3), monosubstituted (e.g., —CH2CH2F) or substituted at a level anywhere in-between fully substituted and monosubstituted (e.g., -CH2CF3). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the direction they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diastereoisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner In either case, the treatment regimen will provide beneficial effects of the drug combination in treating the conditions or disorders described herein.

The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab')2 molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents include, but are not limited to, positron emission tomography (PET), X-ray computed tomography (CT) and magnetic resonance imaging (MRI).

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "patient" does not denote a particular age or sex.

The term "prodrug" refers to a compound that is made more active in vivo. Certain compounds of the present invention may also exist as prodrugs, as described in Hydrolysis in Drug and Prodrug Metabolism: Chemistry, Biochemistry, and Enzymology, Testa, Bernard and Wiley-VHCA, Zurich, Switzerland 2003. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bio-available by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound that is administered as an ester (the "prodrug"), but then is metabolically hydrolyzed to the carboxylic acid, the active entity. Additional examples include peptidyl derivatives of a compound.

The compounds of the invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Stahl, P. Heinrich, Pharmaceutical Salts: Properties, Selection, and Use, Wiley-VCHA, Zurich, Switzerland (2002).

The term "therapeutically acceptable salt" as used herein, represents salts or zwitterionic forms of the compounds of the present invention which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Compositions

The compositions and therapies described herein may be used to effectively kill and/or inhibit pathogens and/or cancers. Specifically, the compositions may kill or inhibit bacterial growth and may, at the same time, aid in healing, including (but not limited to) wound healing. The compositions described herein (anti-pathogenic compositions) may contain therapeutically-effective amounts of one or more amino acids and one or more fatty acids (e.g., UCA and LARG, Decanoic acid and LARG, etc.). The combination of these compounds within the specified ratio ranges may exert a synergistic, not additive, biological mechanism of action that may prevent infection and aid in healing by, e.g., inhibiting pathogen growth and/or enhancing pathogen death (elimination). Furthermore, the compositions described herein may confer greater therapeutic benefit to a treated patient (e.g., a human) than the sequential administration of the substituent compounds. Further, these compositions have been demonstrated to have anti-cancer therapeutic effects, including, but not limited to, inhibiting the growth and/or spread of cancer cells (including tumors).

Thus, the compositions and therapies described herein may be useful for treating symptoms, conditions, and diseases caused by pathogenic infections in a patient (e.g., a human) and/or cancers. Also described herein are pharmaceutical preparations and the medicaments obtained therefrom. The methods and formulations to prepare the compositions described herein are disclosed here.

The combinations of a standard (i.e., canonical) or non-standard (i.e., non-canonical) amino acid (in the D or L isomer), and particularly an amino acid having an electrically charged basic side chain, with an unsaturated or saturated fatty acid (e.g., a C4-C18 fatty acid, a C8-C18, a C4-C20, a C4-C18, etc.) may be used to form a mixture that produces a rapid, potent bactericidal effect in both gram-positive and gram-negative bacteria. The proportion of these mixture components (e.g., amino acid and fatty acid) within the mixture may be optimized for the anti-pathogenic effect.

As used herein, an anti-pathogenic material includes antibacterial (bactericidal) compositions. A bactericide may be considered as a chemical entity producing a bacterial kill rate that is greater than the rate of bacterial growth over time, whereas a bacteriostat may be considered as a chemical entity that inhibits bacterial reproduction but does not directly kill the bacteria.

Examples of unsaturated fatty acids (in addition to those described above), may include, but are not limited to, crotonic acid (CAS Registry Number 107-93-7), myristoleic acid (CAS Registry Number 544-64-9), palmitoleic acid (CAS Registry Number 373-49-9), sapienic acid (CAS Registry Number 17004-51-2), elaidic acid (CAS Registry Number 112-79-8), vaccenic acid (CAS Registry Number 506-17-2), gadoleic acid (CAS Registry Number 29204-02-2), eicosenoic acid (CAS Registry Number 5561-99-9), erucic acid (CAS Registry Number 112-86-7), nervonic acid (CAS Registry Number 506-37-6), linoleic acid (CAS Registry Number 60-33-3, 463-40-1), pinolenic acid (CAS Registry Number 16833-54-8), eleostearic acid (PubChem #5281115), mead acid (CAS Registry Number 20590-32-3), dihomo-gama-linolenic acid (CAS Registry Number 1783-84-2), eicosatrienoic acid (CAS Registry Number 17046-59-2), stearidonic acid (CAS Registry Number 20290-75-9), arachidonic acid (CAS Registry Number 506-32-1), eicosatetraenoic acid (PubChem #231), adrenic acid (CAS Registry Number 28874-58-0), bosseopentaenoic acid (CAS Registry Number 133205-91-1), eicosapentaenoic acid (CAS Registry Number 10417-94-4), ozubondo acid (CAS Registry Number 25182-74-5), tetracosanolpentaenoic acid, docosahexaenoic acid (CAS Registry Number 6217-54-5), and oleic acid (CAS Registry Number 112-80-1).

Examples of saturated fatty acids include (in addition to those described above), but are not limited to, propanoic acid (CAS Registry Number 79-09-04), butanoic acid (CAS Registry Number 107-92-6), pentanoic acid (CAS Registry Number 109-52-4), hexanoic acid (CAS Registry Number 142-62-1), heptanoic acid (CAS Registry Number 111-14-8), octanoic acid (CAS Registry Number 124-07-2), nonanoic acid (CAS Registry Number 112-05-0), decanoic acid (CAS Registry Number 334-48-5), undecanoic acid (CAS Registry Number 112-37-8), dodecanoic acid (CAS Registry Number 143-07-7), tridecanoic acid (CAS Registry Number 638-53-9), tetradecanoic acid (CAS Registry Number 544-63-8), pentadecanoic acid (CAS Registry Number 1002-84-2), hexadecanoic acid (CAS Registry Number 57-10-3), heptadecanoic acid (CAS Registry Number 506-12-7), octadecanoic acid (CAS Registry Number 57-11-4), nonadecanoic acid (CAS Registry Number 646-30-0), eicosanoic acid (CAS Registry Number 506-30-9), heneicosanoic acid (CAS Registry Number 2363-71-5), docosanoic acid (CAS Registry Number 112-85-6), tricosanoic acid (PubChem #17085), tetracosanoic acid (CAS Registry Number 557-59-5), pentacosanoic acid (PubChem #10468), hexacosanoic acid (CAS Registry Number 506-46-7), heptacosanoic acid (PubChem #23524), octacosanoic acid (CAS Registry Number 506-48-9), nonacosanoic acid (PubChem #20245), triacontanoic acid (CAS Registry Number 506-50-3), henatriacontanoic acid (CAS Registry Number 28232-01-8), dotriacontanoic acid (CAS Registry Number 3625-52-3), tritriacontanoic acid (CAS Registry Number 38232-03-0), tetratriacontanoic acid (CAS Registry Number 506-50-3), pentatriacontanoic acid (PubChem #5282595), hexatriacontanoic acid (CAS Registry Number 4299-38-1), and heptatriacontanoic acid (PubChem #5282597).

As mentioned above, in some variations the particular fatty acids of interest herein are C11 fatty acids, such as undecylenic acid. The C11 fatty acids include molecules that include the eleven carbons similar to undecylenic acid and may be combined with other moieties. Other fatty acids of interest may include C4-C20 fatty acids, including in particular unbranched C4-C20 fatty acids, such as (but not limited to): decanoic acid and octanoic acid (e.g., C4-C18, C8-C18, C8-C20, etc.).

A standard (canonical) or non-standard (non-canonical) amino acid is defined as: an organic compound containing an amine (—NH2) and a carboxyl (—COOH) functional group along with a side chain (R group) specific to each amino acid. This includes proteinogenic and non-proteinogenic amino acids. This includes both D and L isomers (enantiomers). To include the following amino acids in both the D and L isomers, but not limited to: alanine, arginine, asparagine, aspartic acid, cysteine, glutamic acid, glutamine, glycine, Histidine, isoleucine, leucine, lysine, methionine, phenylalanine, proline, serine, threonine, tryptophan, tyrosine, valine, selenocysteine, and pyrrolysine Amino acids having electrically charged basic side chains are of particular interest herein. Aliphatic amino acids include: alanine, arginine, asparagine, aspartic acid, cysteine, glutamine, glutamic acid, glycine, isoleucine, lysine, leucine, methionine, serine, threonine, and valine. Non-aliphatic amino acids may include: aromatic amino acids (e.g. phenylalanine, Histidine, tyrosine, tryptophan) and imino amino acids (e.g. proline).

Basic addition salts can be prepared during the final isolation and purification of the compounds by reaction of a carboxy group with a suitable base such as the hydroxide, carbonate, or bicarbonate of a metal cation or with ammonia or an organic primary, secondary, or tertiary amine The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid. The novel compounds described herein can be prepared in a form of pharmaceutically acceptable salts that will be prepared from nontoxic inorganic or organic bases including but not limited to aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally-occurring substituted amines, cyclic amines, and basic ion exchange resins, such as arginine, betaine, caffeine, choline, ethylamine, 2-diethylaminoethano, 1,2-dimethylaminoethanol, ethanolamine, ethylenediamine, N-ethyl-morpholine, N-ethylpiperidine, glucamine, glucosamine, Histidine, hydroxylamine, isopropylamine, lysine, methylglucamine, morpholine, piperazine, piperidine, polyamine resins, procaine, purines, theobromine, triethylamine, trimethylamine, trishydroxylmethyl amino methane, tripropyl amine, and tromethamine.

If the compounds of the invention are basic, salts could be prepared in a form of pharmaceutically acceptable salts that will be prepared from nontoxic inorganic or organic acids including but not limited to hydrochloric, hydrobromic, phosphoric, sulfuric, tartaric, citric, acetic, fumaric, alkylsulphonic, naphthalenesulphonic, para-toluenesulphonic, camphoric acids, benzenesulfonic, benzoic, camphorsulfonic, citric, ethanesulfonic, gluconic, glutamic, isethonic, lactic, maleic, malic, mandelic, methanesulfonic, mucic, nitric, pamoic, pantothenic, phosphoric, and succinic.

While it may be possible for the compounds of the invention to be administered as the raw chemical, it is also possible to present them as a pharmaceutical formulation. Accordingly, the present invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

Formulations that may be suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the present invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds described herein (e.g., anti-pathogenic, and/or anti-cancer compounds) may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the compounds described herein (e.g., anti-pathogenic compounds), the compounds of the invention may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compounds described herein (e.g., anti-pathogenic compounds) may take the form of tablets, lozenges, pastilles, or gels formulated in conventional manner. Such compositions may comprise the active ingredient in a flavored basis such as sucrose and acacia or tragacanth.

The compounds described herein (e.g., anti-pathogenic compounds) may also be formulated in rectal compositions such as suppositories or retention enemas, e.g., containing conventional suppository bases such as cocoa butter, polyethylene glycol, or other glycerides.

The compounds described herein (e.g., anti-pathogenic compounds) may be administered topically, that is by non-systemic administration. This includes the application of a compound externally to the epidermis or the buccal cavity and the instillation of such a compound into the ear, eye and nose, such that the compound does not significantly enter the bloodstream. In contrast, systemic administration refers to oral, intravenous, intraperitoneal and intramuscular administration.

Formulations suitable for topical administration include solid, liquid or semi-liquid preparations suitable for penetration through the skin to the site of infection such as gels, liniments, lotions, creams, ointments or pastes, and drops suitable for administration to the eye, ear or nose. In some examples the active ingredient may comprise, for topical administration, from 0.001% to 40% w/w, for instance from 1% to 5% by weight of the formulation (e.g., 0.001% to 35%, 0.002% to 30%, 0.01% to 25%, 0.05% to 20%, 0.1% to 15%, 0.1% to 12.5%, 0.5% to 10%, 0.5% to 8%, 1% to 7%, 1% to 6%, 1% to 5%, etc.). It may however comprise more than 10% w/w (e.g., 20% or less, 25% or less, 30% or less, 35% or less, 40% or less, 45% or less, 50% or less, etc. and/or in some variations greater than 0.001%, greater than 0.01%, greater than 0.1%, greater than 1%, etc.).

Via the topical route, the pharmaceutical compounds described herein (e.g., anti-pathogenic compounds) may be in the form of liquid or semi liquid such as ointments, or in the form of solid such as powders. It may also be in the form of suspensions such as polymeric microspheres, or polymer patches and hydrogels allowing a controlled release. This topical composition may be in anhydrous form, in aqueous form or in the form of an emulsion. The compounds may be used topically at a concentration of between 0.001% and 10% by weight (e.g., between 0.01% and 1% by weight), relative to the total weight of the composition. In some variations, the compounds may be used topically at greater than 10% by weight (e.g., 20% or less, 25% or less, 30% or less, 35% or less, 40% or less, 45% or less, 50% or less, etc.).

For administration by inhalation, the compounds described herein (e.g., anti-pathogenic compounds) may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Other potential applications may include industrial applications, e.g. "micro-biocides", for use in agriculture, food production, etc.

Preferred unit dosage formulations include those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example, those suitable for oral administration may include flavoring agents.

The compounds described herein (e.g., anti-pathogenic compounds) may be administered orally or via injection at a dose. Tablets or other forms of presentation provided in discrete units may conveniently contain an amount of compound of the invention which is effective at such dosage or as a multiple of the same. For example, compounds described herein (e.g., anti-pathogenic compounds) can be administered at a daily dose of about 0.001 mg/kg to 100 mg/kg of body weight, in 1 to 3 dosage intakes. In some variations, compounds can be used systemically, at a concentration generally of between 0.001% and 10% by weight and preferably between 0.01% and 1% by weight, relative to the weight of the composition.

The mixture of amino acids and fatty acids (e.g., L-Arg and UCA, L-Arg and Decanoic acid, etc.) may be collectively or separately considered the active ingredient (or if separately, active ingredients) that may be combined with the carrier materials to produce a single dosage form will vary depending upon the host treated and the particular mode of administration.

The compounds described herein (e.g., anti-pathogenic compounds) can be administered in various modes, e.g. orally, topically, or by injection. The precise amount of compound administered to a patient may be the responsibility of the attendant physician. The specific dose level for any particular patient may depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (e.g., anti-pathogenic compounds), or a pharmaceutically acceptable salt, ester, or prodrug thereof, in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for pain involving administration of one of the compounds described herein, increased therapeutic benefit may result by also providing the patient with another therapeutic agent for pain. In any case, regardless of the disease, disorder or condition being treated, the overall benefit experienced by the patient may simply be additive of the two therapeutic agents or the patient may experience a synergistic benefit.

Specific, non-limiting examples of possible combinations with the compounds described herein may include use of the compounds together with inert or active compounds, or other drugs including wetting agents, flavor enhancers, preserving agents, stabilizers, humidity regulators, pH regulators, osmotic pressure modifiers, emulsifiers, UV-A and UV-B screening agents, antioxidants, depigmenting agents such as hydroquinone or kojic acid, emollients, moisturizers, for instance glycerol, PEG 400, or urea, antiseborrhoeic or antiacne agents, such as S-carboxymethylcysteine, S-benzylcysteamine, salts thereof or derivatives thereof, or benzoyl peroxide, antibiotics, for instance erythromycin and tetracyclines, chemotherapeutic agent, for example, paclitaxel, antifungal agents such as ketoconazole, agents for promoting regrowth of the hair, for example, minoxidil (2,4-diamino-6-piperidinopyrimidine 3-oxide), non-steroidal anti-inflammatory agents, carotenoids, and especially p-carotene, antpsoriatic agents such as anthralin and its derivatives, eicosa-5,8,11,14-tetraynoic acid and eicosa-5,8,11-triynoic acid, and esters and amides thereof, retinoids, e.g., RAR or RXR receptor ligands, which may be natural or synthetic, corticosteroids or oestrogens, alpha-hydroxy acids and a-keto acids or derivatives thereof, such as lactic acid, malic acid, citric acid, and also the salts, amides or esters thereof, or p-hydroxy acids or derivatives thereof, such as salicylic acid and the salts, amides or esters thereof, ion-channel blockers such as potassium-channel blockers, or alternatively, more particularly for the pharmaceutical compositions, in combination with medicaments known to interfere with the immune system, anticonvulsant agents include, and are not limited to, topiramate, analogs of topiramate, carbamazepine, valproic acid, lamotrigine, gabapentin, phenytoin and the like and mixtures or pharmaceutically acceptable salts thereof. A person skilled in the art will take care to select the other compound(s) to be added to these compositions such that the advantageous properties intrinsically associated with the compounds of the invention are not, or are not substantially, adversely affected by the envisaged addition.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, methods for treating diseases, disorders, conditions, or symptoms in a patient (e.g., a human or animal) in need of such treatment are presented herein, the methods comprising the step of administering to the patient an amount of a compound of the invention effective to reduce or prevent the disease, disorder, condition, or symptom, in combination with at least one additional agent for the treatment of said disorder that is known in the art.

Any of the anti-pathogenic or anti-cancer compositions described herein may be formulated for coating a surface, including coating surfaces of medical devices to prevent bacteria colonization, biofilm formation and the development of hospital acquired infections. The application of medical devices, including their long-term use, can lead to bacterial colonization, biofilm formation, and the development of hospital-acquired bacterial infections, often referred to as nosocomial infections. This includes catheter-related blood stream infection, orthopedic implantations, ventilator associated pneumonia, surgical site infection and catheter associated urinary tract infection. This can result in the need to remove and/or replace the medical device. An anti-pathogenic formulation (e.g., including the amino acid and fatty acid) may be applied to the surface of a medical device in a number of ways, including ionic binding to a surface, passive adsorption, or embedding the formulation within a polymer matrix. The formulation may be used in combination with other molecules, biofilm matrix degrading substances or other antibacterial agents. Any medical device may be coated as described herein, including, e.g., implantable medical devices (stents, shunts, vasoocclusive coils, grafts, pins, plates, etc.) and non-implantable devices (catheters, masks, surgical tools, etc.).

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

FIG. 26 is a table showing a matrix of examples of fatty acids (C4-C20 amino acids) combined with amino acids at a 1:1 molar ratio. Individual cells indicate the ability of each particular combination to form a testable solution and provide an anti-pathogenic/anti-cancer effect. As can be seen, amino acids having an electrically charged basic side chain ("electrically charged side chains—basic"), such as Arginine, Histidine and Lysine, demonstrated a robust ability to form a solution and provide therapeutic effects. In this preliminary analysis, Arginine and Lysine were slightly more robust in forming miscible solutions as compared to histidine; in addition, although virtually all fatty acids demonstrated the ability to combine with any of the amino acids having an electrically charged basic side chain (Arginine, Histidine, Lysine), the C8-C20 fatty acids were slightly more robust. Combinations marked as "no," or putatively indicated by (-), were found to be immiscible when combining just the amino acid and the fatty acid at 1:1 molar ratio (and therefore failed to demonstrate anti-pathogen/anti-cancer effects).

EXAMPLES

One example of a therapeutically effective composition is referred to herein as GS-1. GS-1 is a composition of UCA and LARG in which the molar ratio of UCA:LARG is 5:4 (1:0.76 by weight). GS-1 may be made, for example, by heating and stirring 15 g of LARG into 75 g of water at 65 degrees C. until fully dissolved, and then adding 19.8 g of UCA while heating and stirring.

Figure 13:
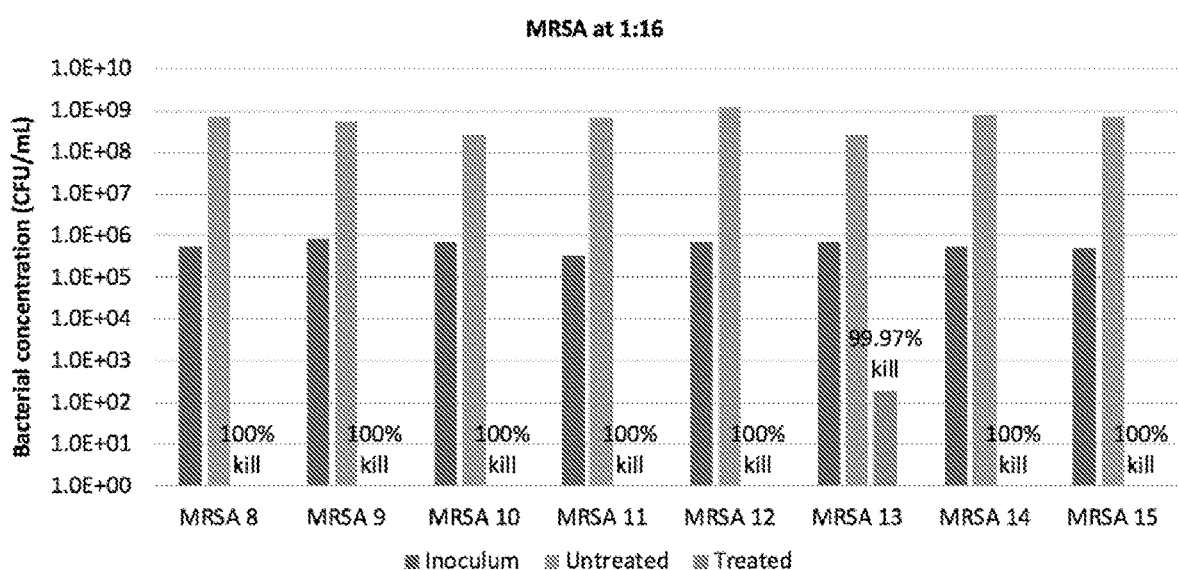
FIG. 13 is a graph showing the in vitro efficacy of one variation of a compound as described herein (referred to as "GS-1") against eight isolates of methicillin-resistant *Staphylococcus aureus* (MRSA) at a drug dilution of 1:16. MRSA is gram-positive.

FIG. 13 shows the therapeutic efficacy of GS-1 against eight isolates of methicillin-resistant *Staphylococcus aureus* (MRSA) at a drug dilution of 1:16. MRSA is gram-positive. In FIG. 13, GS-1 resulted in almost universal, complete (100%) killing of the MRSA isolates. In this example, bacteria (MRSA isolates) are put onto fresh plates and allowed to grow for 30 hours. A suspension inoculum is made from the plates (e.g., a 1 McFarland solution in sterile water), from which the turbidity may be optically read. A standard inoculum may then be cultured in media and 100 µL of that solution combined with 100 µL of drug product and grown at various dilutions for 16-20 hrs. Duplicates may then be examined (e.g., following pelleting at 7,000 RPM for 15 min, resuspended in PBS and serial dilutions plated and grown for 24 hrs.). Duplicate plates at multiple dilutions may then be imaged and colonies counted. Treated samples were compared with untreated samples (e.g., in which water without UCA and LARG included) and inoculum (showing cell viability).

Figure 14:
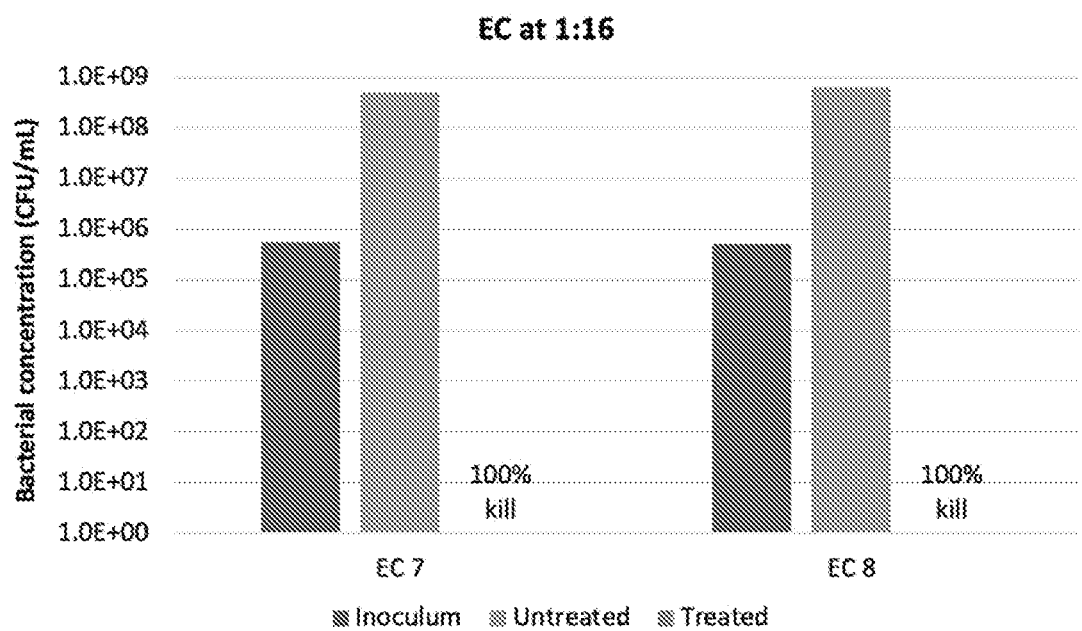
FIG. 14 is a graph illustrating the efficacy of the GS-1 compound against two isolates of *Escherichia coli* (EC) at a drug dilution of 1:16. EC is gram-negative.

FIG. 14 illustrates the therapeutic effect of the GS-1 composition against *Escherichia coli* (EC). Two isolates of *Escherichia coli* (EC) were examined at a drug dilution of 1:16. As shown the GS-1 composition resulted in complete (100%) killing of the bacteria at this dilution. The data was collected as described above, showing a comparison between untreated bacteria and inoculum.

Figure 15:
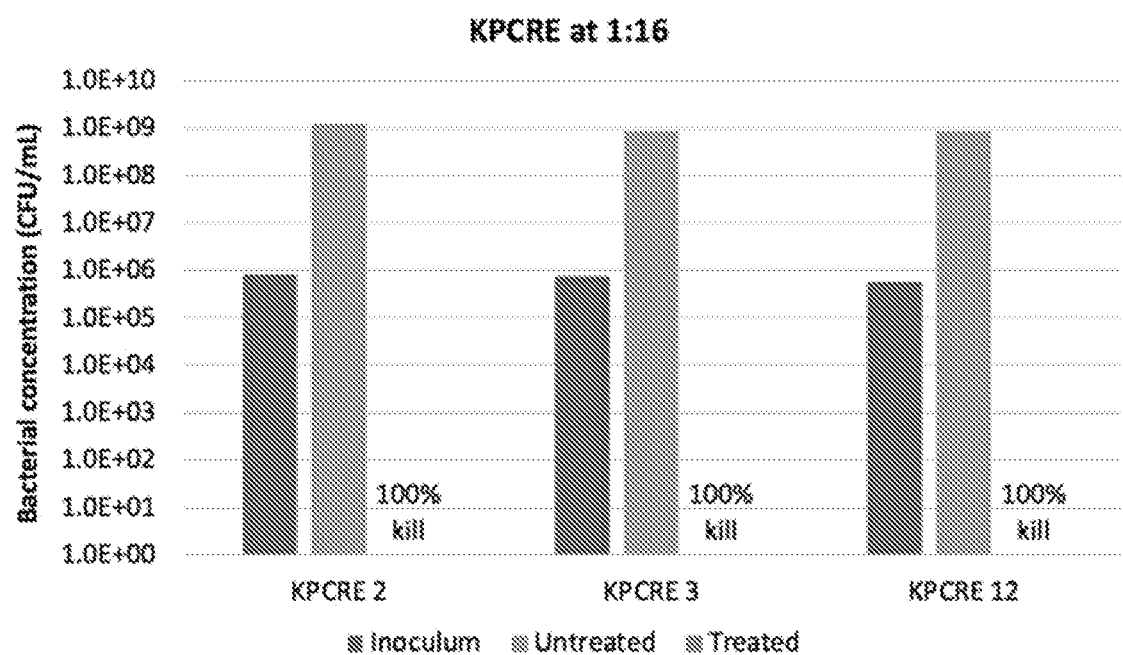
FIG. 15 is an example of a graph illustrating the in vitro efficacy of GS-1 against three isolates of CRE-positive *Klebsiella pneumoniae* (KPCRE) at a drug dilution of 1:16. KPCRE is gram-negative.

Similarly, FIG. 15 illustrates the in-vitro efficacy of GS-1 against three isolates of CRE-positive *Klebsiella pneumoniae* (KPCRE) at a drug dilution of 1:16. As with EC and MRSA, GS-1 resulted in complete killing (100%) of the bacteria for each of the isolates.

Figure 16:
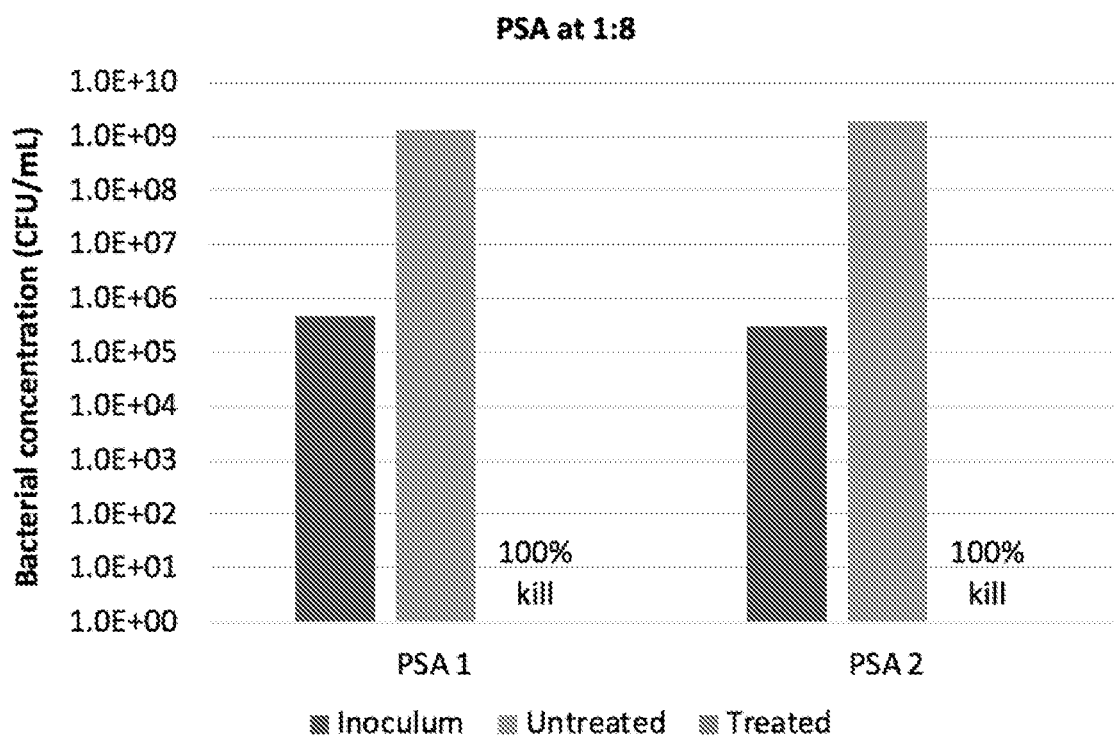
FIG. 16 illustrates the in vitro efficacy of GS-1 against two isolates of *Pseudomonas aeruginosa* (PSA) at a drug dilution of 1:8. PSA is gram-negative.

FIG. 16 shows a similar effectiveness of GS-1 against two isolates of *Pseudomonas aeruginosa* (PSA) at a drug dilution of 1:8. In this example, all (100%) of the bacteria were killed. Similar results (>99.9% killed) were seen at a 1:16 dilution (not shown).

Figure 17:
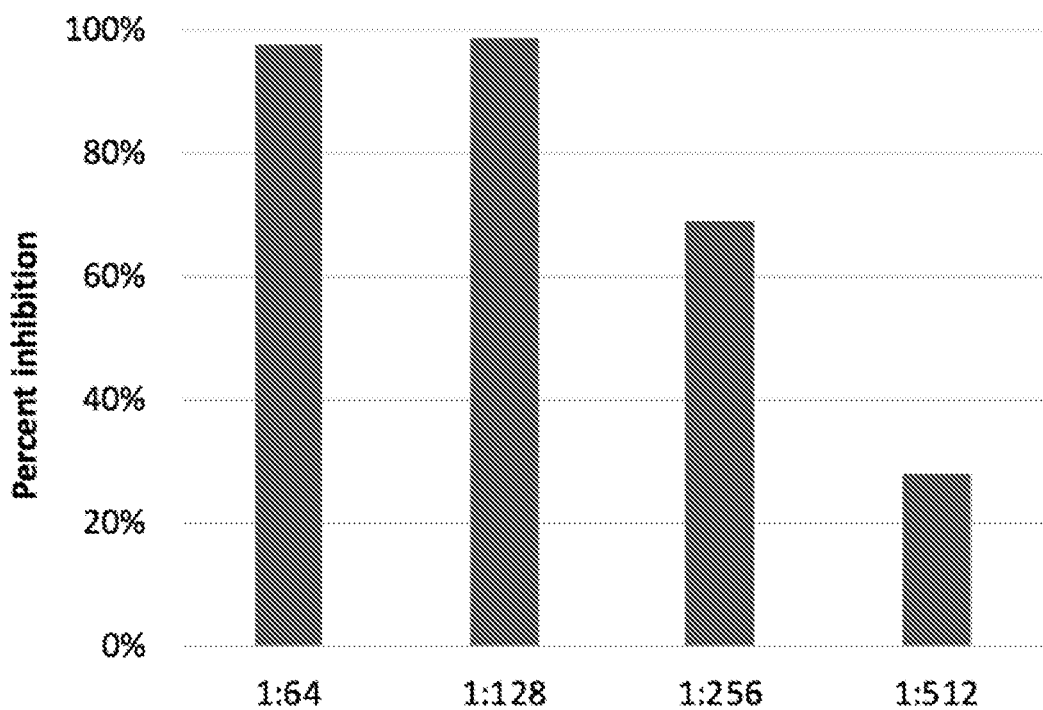
FIG. 17 shows the in vitro efficacy of GS-1 against C6 rat glioma cancer cells as a function of drug dilution.

GS-1 was also found to have anti-cancer activity. For example, cultured rat glioma cancer cells were treated with GS-1 at increasingly dilute concentrations, resulting in inhibition of all or nearly all of the cancer cells at concentrations as dilute as 1:128, and significant inhibition at lower (e.g., 1:256 and 1:512) dilution, as shown in FIGS. 17 and 18A-18E. For example, in FIG. 17, rat glioma cancer cells were cultured to approximately 90% confluence, trypsinized, and seeded at high titer (e.g., 4500 per well), allowed to settle and adhere overnight before treatment with GS-1 at particular dose dilutions. Serial cellular dilutions for each GS-1 dose were examined, and treated cells were cultured 24 hrs., then the media (including the GS-1) was replaced with fresh media and an MTS assay (based on the reduction of the MTS tetrazolium compound by viable cells) was performed to allow quantification of healthy cells by colorimetric change. FIG. 17 shows the percentage of inhibition of cancer cell proliferation as compared with untreated cells.

Figure 18A:
FIGS. 18A-18E illustrate microscopic imaging of in vitro efficacy for GS-1 against C6 rat glioma cancer cells as a function of drug dilution.
Figure 18B:
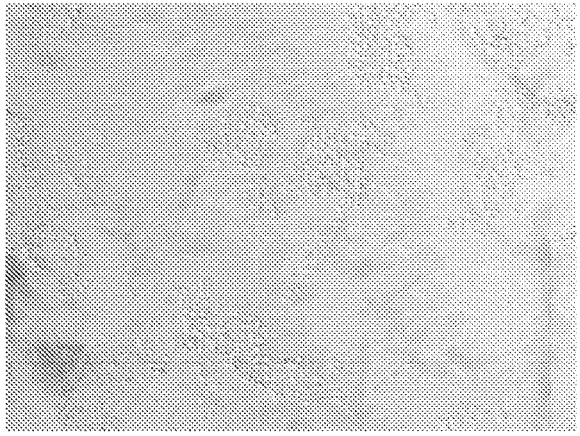
Figure 18C:
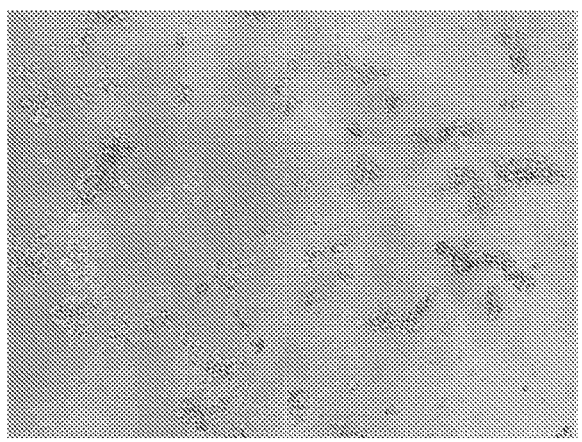
Figure 18D:
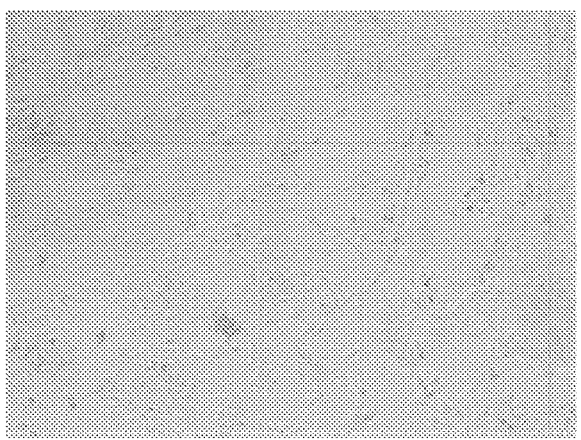
Figure 18E:
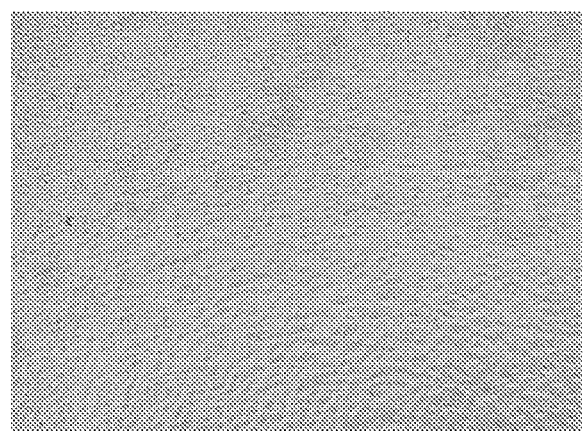

FIGS. 18A-18E show images of cancer cells treated with increasing dilutions of GS-1 (FIGS. 18A-18D) and untreated (FIG. 18E). Each image is a microscopic view showing in vitro efficacy of GS-1 in killing C6 rat glioma cancer cells, as a function of drug dilution. Each of FIGS. 18A-18E show a fluorescent image using a vital (e.g., PI) stain that is overlaid with a non-fluorescent image to visually show unhealthy cells (dead or dying cancer cells) versus healthy cells. As shown in FIGS. 18A-18D, unhealthy cells uptake the PI stain and fluoresce, whereas healthy cells do not. In agreement with FIG. 17, the higher dilutions of GS-1 (1:64 and 1:128) show near-complete efficacy in killing the cancer cells, with almost all cells fluorescing, while at the higher dilutions (e.g., 1:256 and 1:512) there is decreasing efficacy, with fewer cells fluorescing. No cells in the untreated control, FIG. 18E, are fluorescing. Each of these images were taken at the same exposure to allow comparison.

Companion studies, examining the effect of GS-1 on 'normal' cells, including healthy animal cells showed no effect, including at high (undiluted) concentrations, as compared to cancer cells.

Animal studies have also been performed to establish the in vivo safety and efficacy of GS-1. In one example study, 16 rats were dermally abraded on a 4×4 cm area and then infected with methicillin resistant *Staphylococcus aureus* (MRSA). After 24 h, half of the rats were treated with GS-1, and half were treated with saline (untreated controls), twice daily for 7 days. At the end of 7 days, skin swabs and tissue punches at the site of infection were collected and analyzed for evidence of infection (efficacy), and blood was drawn and analyzed for evidence of toxicity (safety). All rats treated with GS-1 showed no signs of infection after 7 days, and showed no signs of toxicity or side-effects compared to the untreated control animals.

Figures 19, 20:
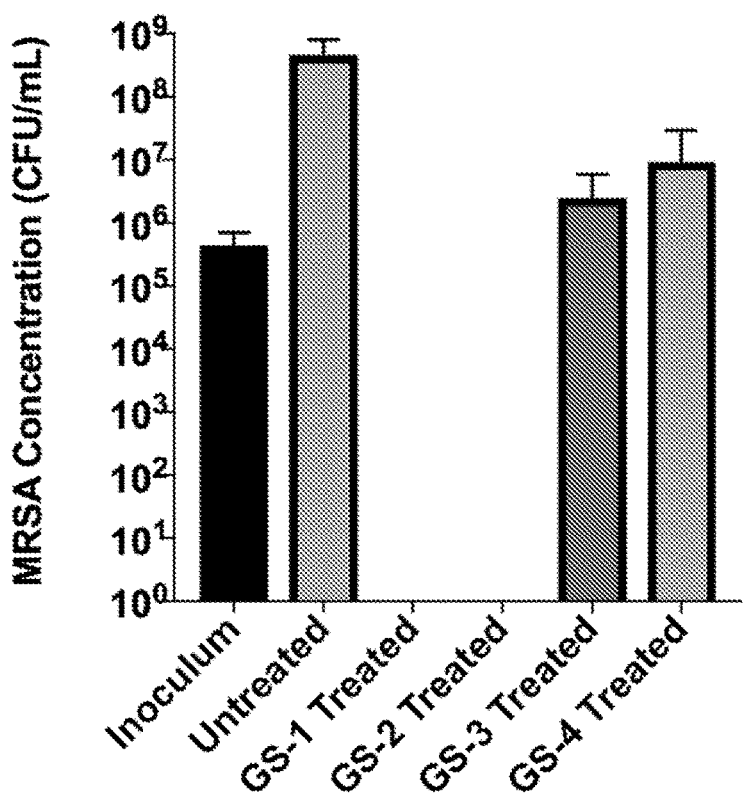
FIG. 19 is a table showing the results of a freezer stability study for exemplary compositions as described herein.
FIG. 20 is a graph illustrating the therapeutic effects of four compositions of a fatty acid:amino acid at about a 1:0.76 (fatty acid:amino acid) ratio by weight when diluted and used to treat MRSA. GS-1 corresponds to UCA:LARG (at a molar ratio of 1:0.8) as described above, at a dilution of 1:128 of an approximately 32% w/w mixture, resulting in a concentration of about 0.25% total active pharmaceutical ingredients (APIs). GS-2 corresponds to a mixture of Decanoic acid:LARG, (having a molar ratio of about 1:0.8) at a dilution of 1:128 of an approximately 32% w/w mixture, resulting in a concentration of about 0.25% w/w total APIs. GS-3 corresponds to a mixture of Octanoic acid:LARG, (having a molar ratio of about 1:0.6) at a dilution of 1:128 of an approximately 32% w/w mixture, resulting in a concentration of about 0.25% w/w total APIs. GS-4 corresponds to a mixture of Linoleic acid:LARG at a concentration of about 1.64 mg/mL (0.16% w/w) total APIs, having a molar ration of about 1:6.1.

As mentioned above, in general the compositions described herein may include one or more fatty acids and one or more amino acids in a fatty acid:amino acid molar ratio of between about 1:0.6 to about 1:1.6. FIGS. 1-18 illustrate compositions in which the fatty acid is UCA and the amino acid is LARG, however, the compositions and methods described herein are not limited to UCA and LARG. For example, FIG. 20 shows a comparison of a UCA/LARG composition ("GS-1"), with mixtures of Decanoic acid/LARG ("GS-2"), Octanoic acid/LARG ("GS-3"), and Linoleic acid/LARG ("GS-4"), each of which showed significant anti-pathogenic activity at comparable concentrations, and as compared to untreated conditions and an inoculum control. For example, in each of these examples in FIG. 20, the fatty acid to amino acid in the compositions was at a ratio of about 1:0.76 (fatty acid:amino acid) by weight when diluted and used to treat MRSA. GS-1, GS-2 and GS-3 all had fatty acid:amino acid aqueous mixtures with approximately 32% w/w of total active pharmaceutical ingredients (APIs), which were diluted at 1:128 in water, resulting in a concentration of about 0.25% w/w total APIs. GS-4 had a concentration of about 1.64 mg/mL (0.16% w/w) total APIs. In FIG. 20, GS-1 and GS-2 resulted in near-total bactericidal effect on the MRSA (shown by the lack of bar), while GS-3 and GS-4 had a substantial reduction in MRSA compared to untreated control. Note that GS-4 was used at a lower concentration than GS-1 to GS-3 (e.g., 0.16% w/w total APIs, rather than 0.25% w/w for GS-1 to GS-3). All of these results indicated an efficacy that is comparable or superior to commercially available antibiotics, such as the topical antibiotic mupirocin ("Bactroban").

Figure 21:
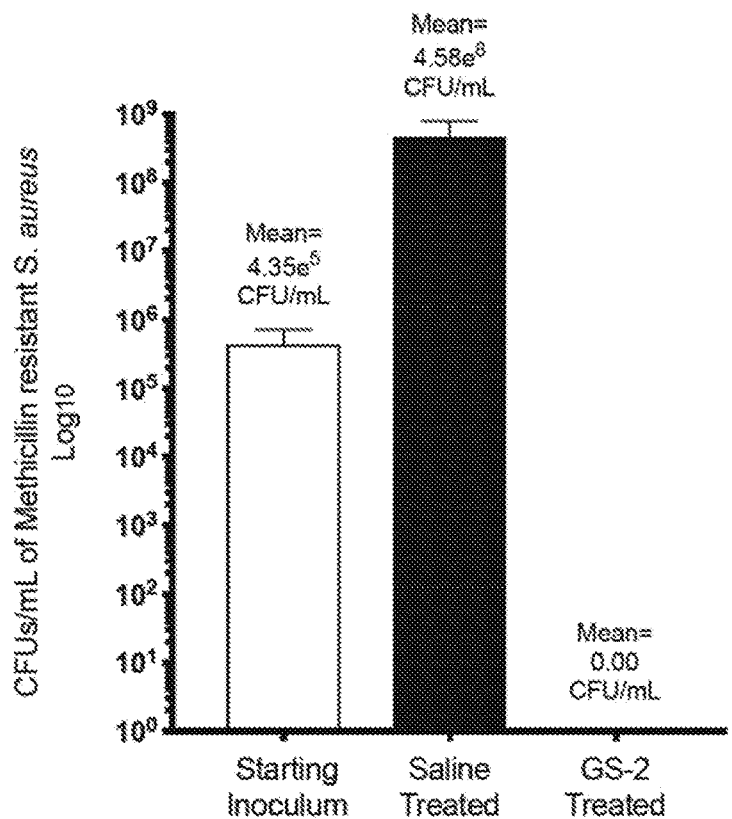
FIG. 21 is a graph showing activity of GS-2 (Decanoic acid:LARG, at a concentration of about 0.25% w/w total API and a molar ratio of about 1:0.8) against MRSA compared to saline-treated control for six clinical isolates for 24 hours. The Decanoic acid:LARG composition produced a bactericidal effect in 100% of the isolates.
Figure 22:
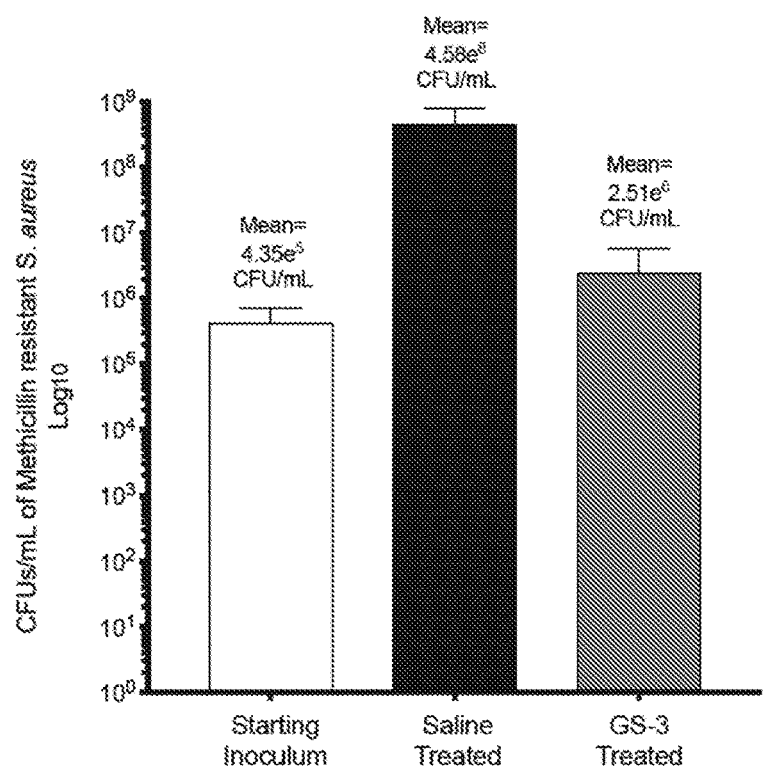
FIG. 22 is a graph showing activity of GS-3 (Octanoic acid:LARG, at a concentration of about 0.25% w/w total API and a molar ratio of about 1:0.6) against MRSA compared to saline-treated control for six clinical isolates for 24 hours. The Octanoic acid:LARG composition produced an inhibitory effect in 66.7% of the isolates and a bacteriostatic effect in 33.3%.
Figure 23:
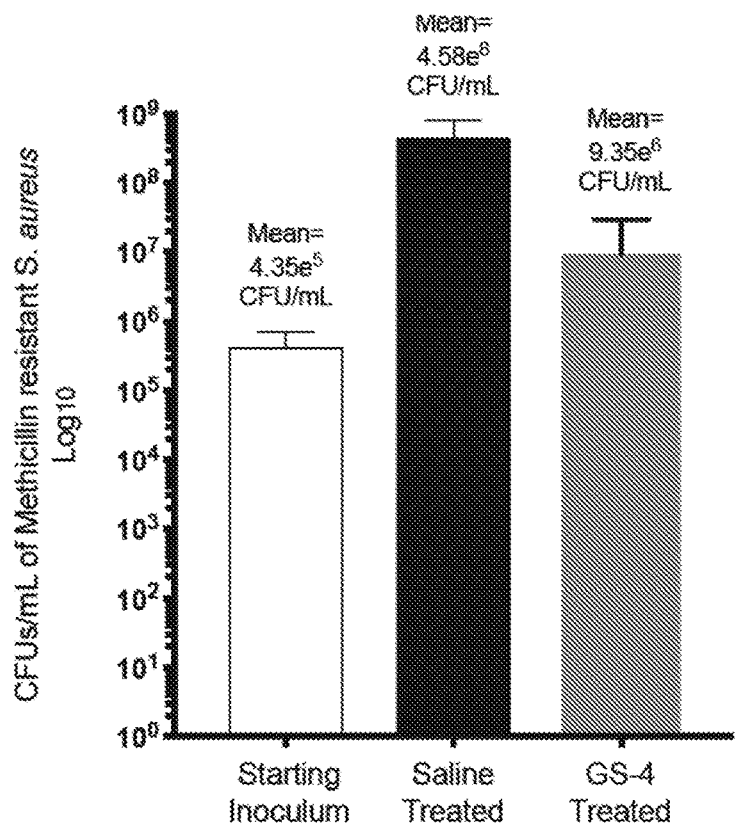
FIG. 23 is a graph showing activity of GS-4 (Linoleic acid:LARG, at a concentration of about 0.16% w/w total API and a molar ratio of about 1:6.1) against MRSA compared to saline-treated control for six clinical isolates for 24 hours. GS-4 produced a bactericidal effect in 50% of the isolates and an inhibitory effect in 50%.

FIGS. 21-23 illustrate specific results for each of GS-2, GS-3 and GS-4. FIG. 21 shows the activity of a composition of Decanoic acid and LARG (at a 1:0.76 ratio by weight). In FIG. 21, the treated concentration was about 2.51 mg/mL (0.25% w/w) of total API (e.g., of Decanoic acid and LARG). Six individual clinical isolates were treated with GS-2 in solution for 24 hours, and resulted in complete killing of all of the MRSA present (e.g., 100% bactericidal).

FIG. 22 shows a similar assay using a composition including a 1:0.76 w/w ratio of Octanoic acid to LARG (GS-3). The concentration of the Octanoic acid/LARG in the treatment solution was 2.52 mg/mL (0.25% w/w) for the total API, and was added to six clinical MRSA isolates and treated for 24 hours. In this assay the GS-3 (Octanoic acid/LARG) produced an inhibitory effect in 66.7% of the isolates and a bacteriostatic effect in 33.3%. The concentration of the Octanoic acid/LARG composition may be increased to get a complete bactericidal effect.

FIG. 23 shows an example in which a mixture of Linoleic acid and LARG (GS-4) were combined. In this example, the C18 Linoleic acid was used to treat six MRSA clinical isolates at a concentration of 1.64 mg/mL (0.16% w/w) total API for 24 hours in solution. The GS-4 mixture resulted in a bactericidal effect in 50% of the isolates and an inhibitory effect in 50%.

Figure 24:
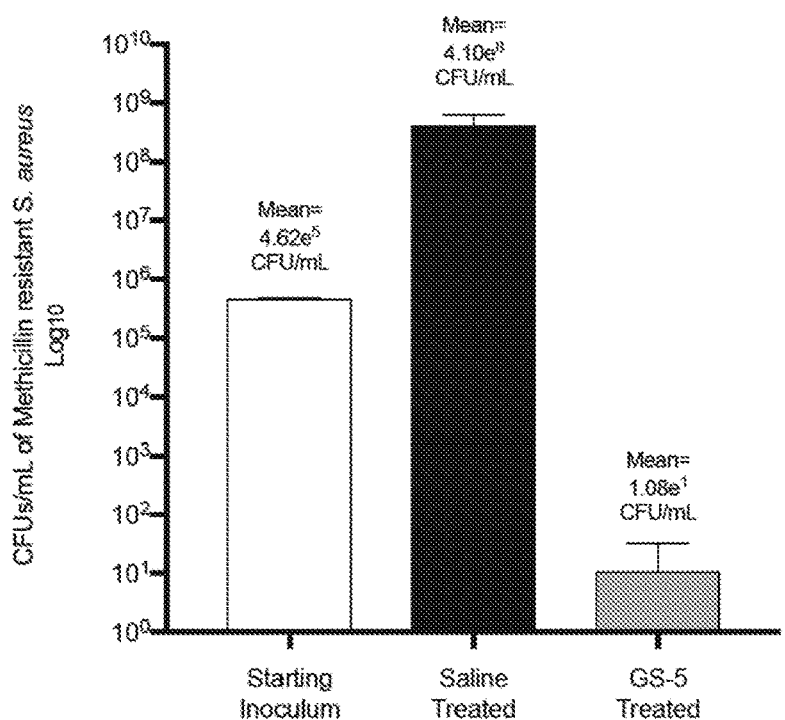
FIG. 24 is a graph showing activity of GS-5 (UCA: Lysine, at a concentration of about 0.25% w/w total API and a molar ratio of about 1:1.0) against MRSA compared to saline-treated control for five clinical isolates for 24 hours. GS-5 produced a bactericidal effect in all of the isolates at this concentration.

FIG. 24 illustrates one example of a composition of fatty acid and amino acid having a ratio of 1:0.76 w/w, as described above. In this example, the fatty acid is UCA and the amino acid is Lysine (GS-5). As shown in FIG. 24, five clinical isolates of MRSA were treated with GS-5 (UCA/Lysine) at a concentration of 2.46 mg/mL (0.25% w/w) total API in a solution for 24 hours. The GS-5 composition resulted in a bactericidal effect in all isolates, as shown (note the logarithmic scale).

Figure 25:
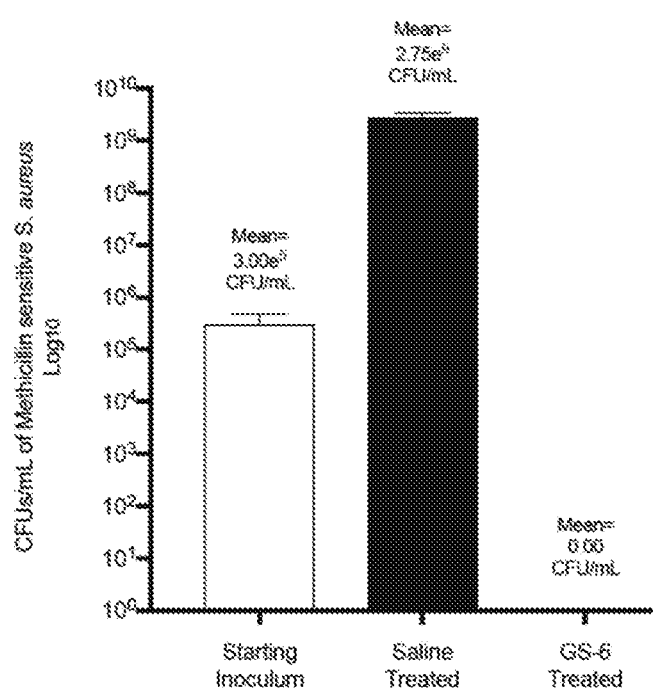
FIG. 25 is a graph showing activity of GS-6 (UCA: Histidine), at a molar ratio of about 1:0.8 (e.g., 5:4). The weight ratio is about 1:0.76. The use of Histidine as the amino acid also showed a significant amount of activity, as shown. Preliminary results suggest a similar range of efficacy as seen with UCA:Lysine and UCA:L-Arginine).

Similarly, FIG. 25 illustrates an example of a composition of fatty acid and amino acid, where the amino acid is Histidine. The complex of Histidine and UCA may have a ratio of 1:0.76 w/w (e.g., a molar ratio of about 1.25:1 UCA:Histidine). As shown in FIG. 25, the Histidine had a clear bactericidal and bacteriostatic effect against Methicillin sensitive *Staphylococcus aureus* (MSSA). In this example, four clinical isolates were treated with GS-6 (UCA:Histidine as descried above) at a concentration of 2.71 mg/ML (0.25% w/w) total API in solution for 24 hours. GS-6 produced a bactericidal effect in all of the isolates (100%), as shown in FIG. 25.

Thus, based on the data and other experiments in which the amino acids were varied with positive charged (basic at physiological pH) fatty acids (e.g., UCA:L-ARG, UCA:Lysine, and UCA:Histinde) whereas other amino acids were less effective (or ineffective, such as D-Arginine, and other non-charged amino acids) in evoking a bactericidal effect. Thus in some variations, the amino acid may be limited to a charged (and particularly the positively charged) amino acids, such as amino acid having an electrically charged basic side chain.

Combination with Other Active Agent(s)

In general, any of the therapeutic compositions described herein may include one or more additional components that may act as or enhance the activity of the fatty acid and amino acid. For example, any of the therapeutic compositions described herein may be combined with one or more additional active ingredients to provide different or enhanced properties, such as enhanced efficacy.

In some variations the compositions described herein may include an additional agent that disrupts cell membranes. In some variations, the compositions described herein may include an antibiotic, such as a polymyxin (e.g. polymyxin B or polymyxin E) to further enhance efficacy. In general, the therapeutic compositions described herein may be combined with one or more non-ribosomal peptides (e.g., actinomycin, bacitracin, daptomycin, vancomycin, teixobactin, tyrocidine, gramicidin, zwittermicin A, ACV-Tripeptide, epothilone, bleomycin, ciclosporin (Cyclosporine A), etc.). The addition of an additional component, such as polymyxin, with the compositions described herein may permit a substantially lower amount of antibiotic to be used and/or may dramatically potentiate the efficacy of the antibiotic.

Figure 27:
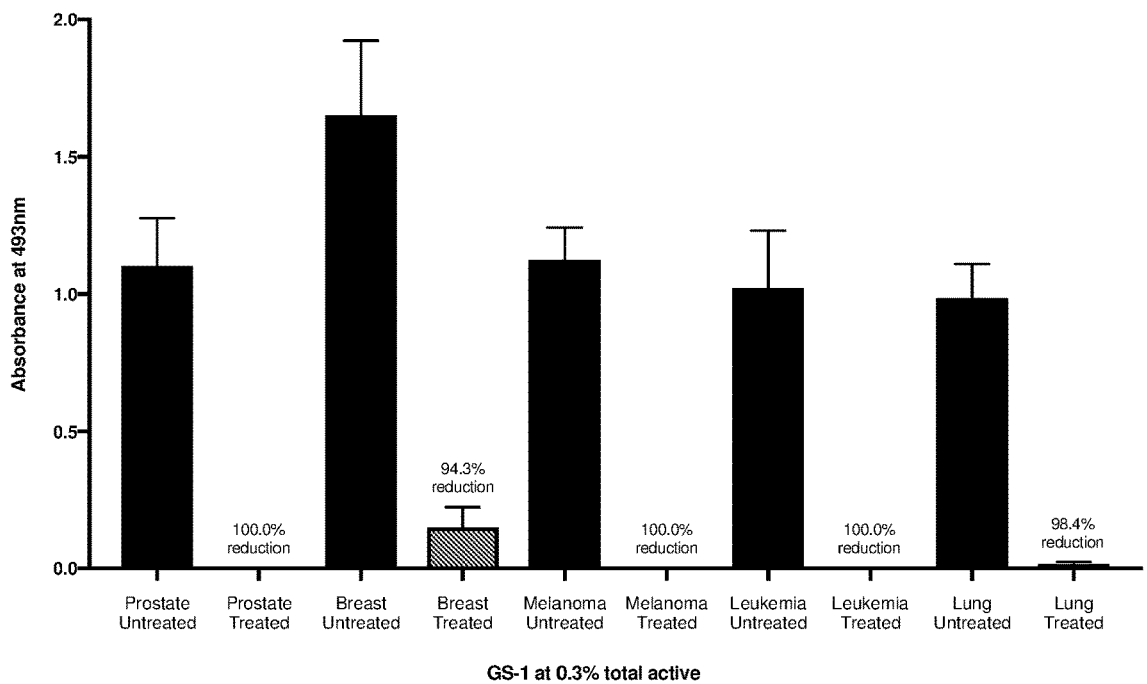
FIG. 27 is a graph showing anti-cancer efficacy of the therapeutic composition of an agent comprising a mixture of fatty acid and amino acid as described herein, in which the molar ratio of fatty acid:amino acid is between about 1:0.6 and about 1:1.6; in this example, the agent is a solution of GS-1 (LARG and UCA) tested against human cancer cells, showing a working drug concentration of 0.3% w/w.

As discussed above, the compositions described herein have both anti-pathogenic (e.g., anti-bactreial, anti-viral, anti-fungal, etc.) efficacy as well as anti-cancer efficacy. For example, FIG. 27 shows a graph summarizing test results for one example of a composition as described herein, including LARG and UCA (GS-1) in an approximately 1:1 molar ratio. In this example, in vitro activity against human cancer cells is shown. The graph shows untreated and treated values for each of a variety of cancer cell lines. All results are for a working drug concentration of 0.3% w/w. All of the examined cancer cell lines showed a marked reduction in cancer cell viability 24 hours after exposure to the composition, as measured by optical absorbance (e.g., absorbance at 493 nm). In this example, each of prostate cancer cells, breast cancer cells, melanoma cancer cells, Leukemia cells and lung cancer cells showed a reduction following treatment with 0.3% of the GS-1 solution.

FIGS. 28-32 illustrate the anti-cancer effects of one example of the therapeutic composition (e.g., GS-1) described herein. Similar results are seen, or predicted to be seen, with the other therapeutic compositions comprising a mixture of a fatty acid:amino acid in a molar ratio of between about 1:0.6 to about 1:1.6, including for virtually any C4-C20 fatty acid and amino acid (including Arginine, Histidine, and/or Lysine, etc.).

Figure 28:
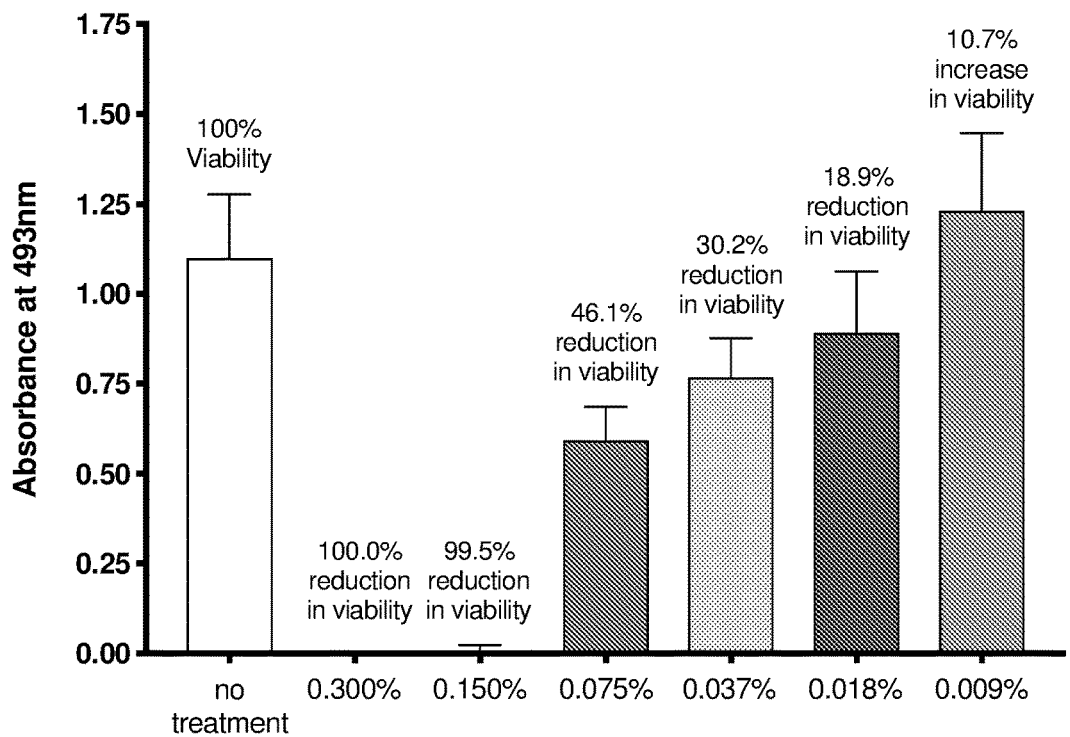
FIG. 28 is a graph showing the anti-cancer effect of an example of the mixture of fatty acid and amino acid as described herein, in which the molar ratio of fatty acid:amino acid is between about 1:0.6 and about 1:1.6 (in this example, LARG and UCA, GS-1) at different concentrations on cultured PC3 human prostate cancer cells following a 24 hour incubation with various concentrations of the agent.
Figure 29:
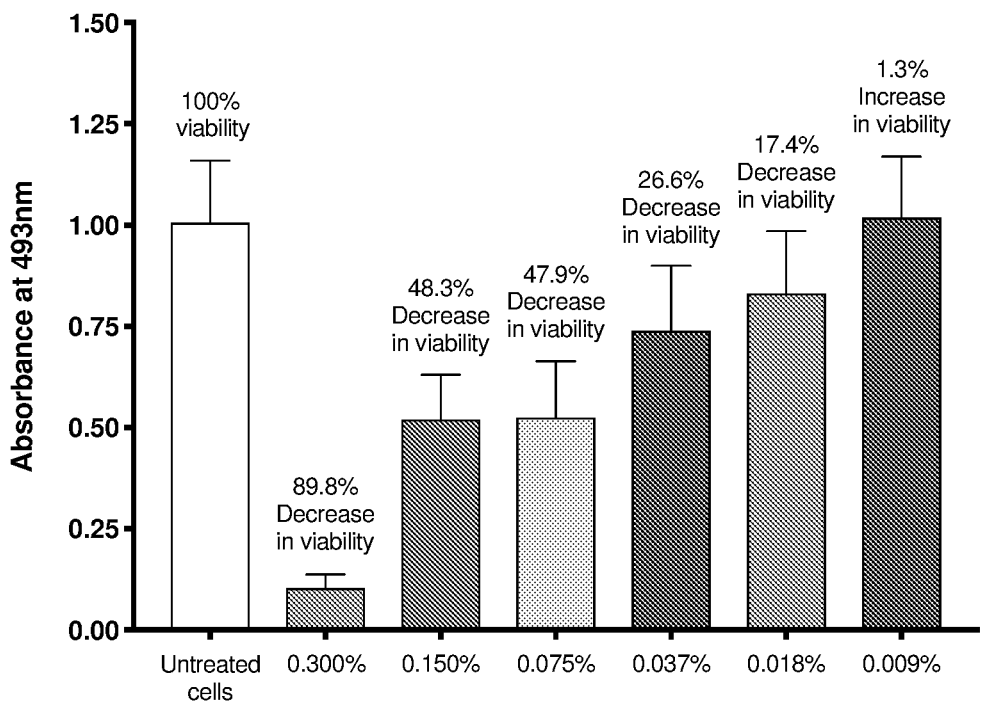
FIG. 29 is a graph showing the anti-cancer effect of an example of the mixture of fatty acid and amino acid as described herein, in which the molar ratio of fatty acid:amino acid is between about 1:0.6 and about 1:1.6 (in this example, LARG and UCA, GS-1) at different concentrations on cultured MCF7 breast cancer cells following a 24 hour incubation with various concentrations of the agent.

For example, FIG. 28 is a graph illustrating the results of a composition of a mixture of a fatty acid:amino acid in a molar ratio of between about 1:0.6 to about 1:1.6 showing an anti-cancer efficacy on PC3 human prostate cancer cells in culture. The mixture is a mixture of LARG and UCA, treating human prostate cancer cells. In FIG. 28, there was a complete reduction in viability of cancer cells following 24 hours of treatment using 0.30% of the composition (GS-1) and a 99.5% reduction in viability of cultured cancer cells using 0.150% of the composition. PC3 human prostate cancer cells were seeded onto sterile 96 well plates at 7000 cells per well. After 24 hours of growth, the cells were further incubated at 37 degrees Celsius with dilutions of GS-1 (GS-1-2) from a stock concentration of 30% for 24 hours. After incubation, the media and test article were removed and replaced with fresh pre-warmed media. 20 μL of MTS was added to each well containing 100 μL of media and was incubated for 2 hours. After incubation, the plate was analyzed on a 96 well colorimetric plate reader. Blank subtraction was performed on all data using 100 μL media and 20 μL MTS absent cells (n=12 wells per treatment and n=24 wells no treatment). Error bars are standard deviation.

Similar results were seen with cultured breast cancer cells. For example, in FIG. 29, the graph shows MTS cell viability from an assay in which MCF7 breast cancer cells were seeded onto sterile 96 well plates at 7000 cells per well. After 24 hours of growth, the cells were further incubated at 37 degrees Celsius with dilutions of GS-1 (GS-1-2) from a stock concentration of 30% for 24 hours. After incubation, the media and test article were removed and replaced with fresh pre-warmed media. 20 μL of MTS was added to each well containing 100 μL of media and was incubated for 2 hours. After incubation, the plate was analyzed on a 96 well colorimetric plate reader. Blank subtraction was performed on all data using 100 μL media and 20 μL MTS absent cells (12 wells per treatment, 12 wells were untreated). Incubation with 0.300% of the composition (GS-1) showed an 89.8% decrease in cultured breast cancer cell viability.

Figure 30:
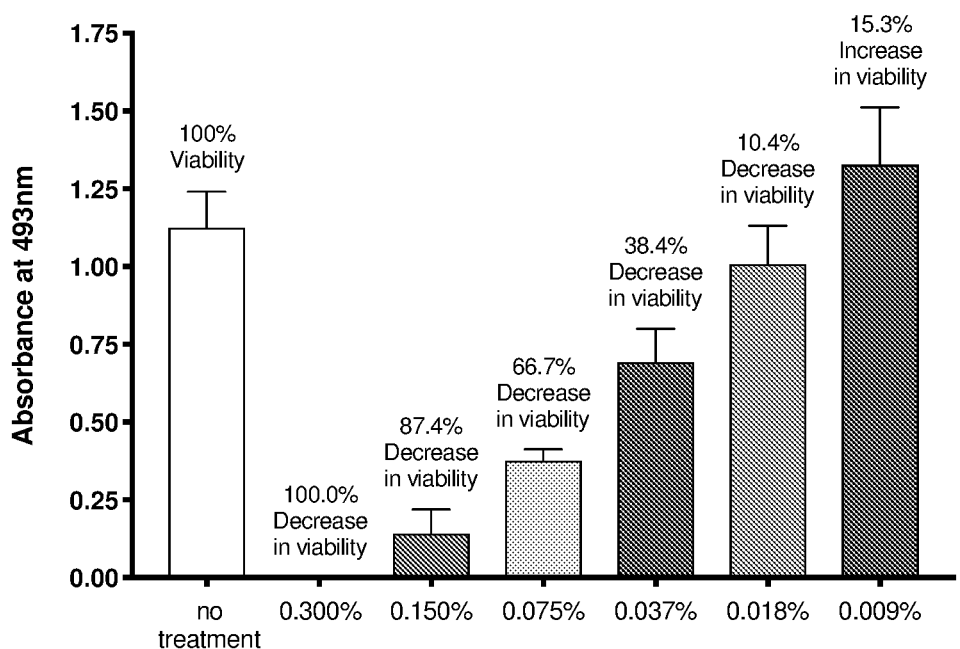
FIG. 30 is a graph showing the anti-cancer effect of an example of the mixture of fatty acid and amino acid as described herein, in which the molar ratio of fatty acid:amino acid is between about 1:0.6 and about 1:1.6 (in this example, LARG and UCA, GS-1) at different concentrations on cultured MM170 human melanoma cancer cells following a 24 hour incubation with various concentrations of the agent.
Figure 31:
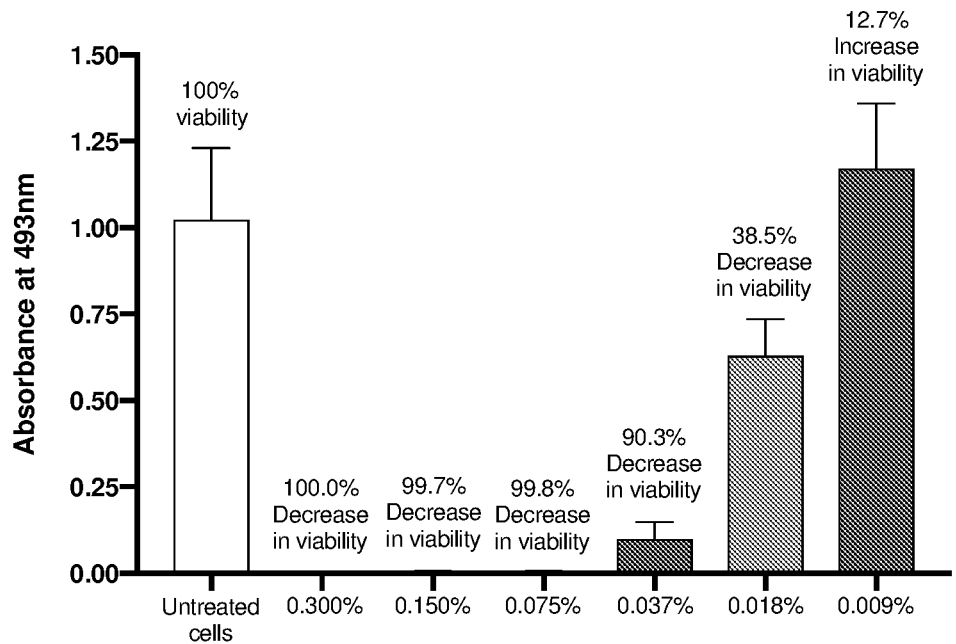
FIG. 31 is a graph showing the anti-cancer effect of an example of the mixture of fatty acid and amino acid as described herein, in which the molar ratio of fatty acid:amino acid is between about 1:0.6 and about 1:1.6 (in this example, LARG and UCA, GS-1) at different concentrations on cultured U937 human leukemia cancer cells following a 24 hour incubation with various concentrations of the agent.

FIG. 30 shows the results of treatment of cultured human skin cancer (MM170 Human Melanoma cells) following 24 hour treatment. In FIG. 30, MM170 human melanoma cells were seeded onto sterile 96 well plates at 7,000 cells per well. As above, after 24 hours of growth, the cells were further incubated at 37 degrees Celsius with dilutions of GS-1 (from a stock concentration of 30%) for 24 hrs. After incubation, the media and test article were removed and replaced with fresh pre-warmed media. 20 μL of MTS was added to each well containing 100 μL of media and was incubated for 2 hrs. After incubation the plate analyzed on a 96 well colorimetric plate reader. Blank subtraction was performed on all data using 100 μL media+20 μL MTS absent cells. Treated wells=12 wells. No treatment wells=24. Error bars represent standard deviation. Complete (e.g., 100%) decrease in viability was seen using a 0.300% concentration.

Treatment of cultured human leukemia cells showed a similar trend; incubation with a solution of 0.075% resulted in a 99.8% decrease in viability of the cultured cells. U937 human leukemia cells were seeded onto sterile 96 well plates at 7,000 cells per well. After 24 hours of growth, the cells were further incubated at 37 degrees Celsius with dilutions of GS-1 (from a stock concentration of 30%) for 24 hrs. After incubation, the media and test article were removed and replaced with fresh pre-warmed media. 20 μL of MTS was added to each well containing 100 μL of media and was incubated for 2 hrs. After incubation the plate analyzed on a 96 well colorimetric plate reader. Blank subtraction was performed on all data using 100 μL media and 20 μL MTS absent cells. Treated wells: n=4 (3 wells per n; 12 total wells). No treatment wells n=8 (3 wells per n; 24 wells total).

Figure 32:
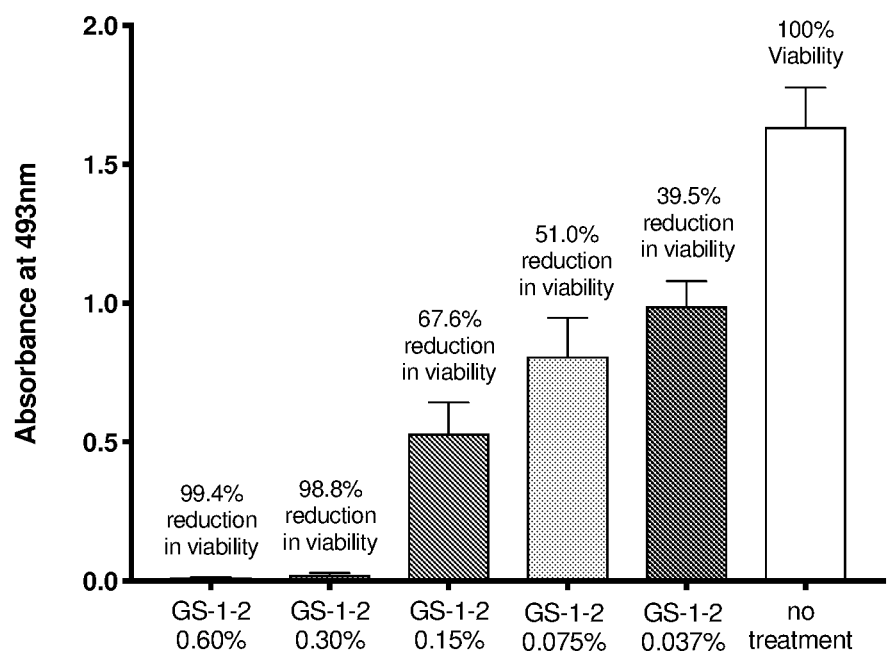
FIG. 32 is a graph showing the anti-cancer effect of an example of the mixture of fatty acid and amino acid as described herein, in which the molar ratio of fatty acid:amino acid is between about 1:0.6 and about 1:1.6 (in this example, LARG and UCA, GS-1) at different concentrations on cultured A549 human lung cancer cells following a 24 hour incubation with various concentrations of the agent.

Cultured human lung cancer cells (A549 Human Alveolar Adenocarcinoma Cells) also showed a nearly complete reduction (e.g., to 98.8%) in viability following treatment with a 0.30% solution of the GS-1 therapeutic composition, As shown in FIG. 32, A549 human lung cancer cells were seeded onto sterile 96 well plates at 7,000 cells per well. As described above, after 24 hours of growth, the cells were further incubated at 37 degrees Celsius with dilutions of GS-1 (from a stock concentration of 30%) for 24 hrs. After incubation, the media and test article were removed and replaced with fresh pre-warmed media. 20 μL of MTS was added to each well containing 100 μL and incubated for 2 hrs. After incubation the plate analyzed on a 96 well colorimetric plate reader. Blank subtraction was performed on all data using 100 μL media and 20 μL MTS absent cells. n=12 wells (3 replicates×4) per treatment. n=35 wells no treatment. Error bars are standard deviation.

Figure 33:
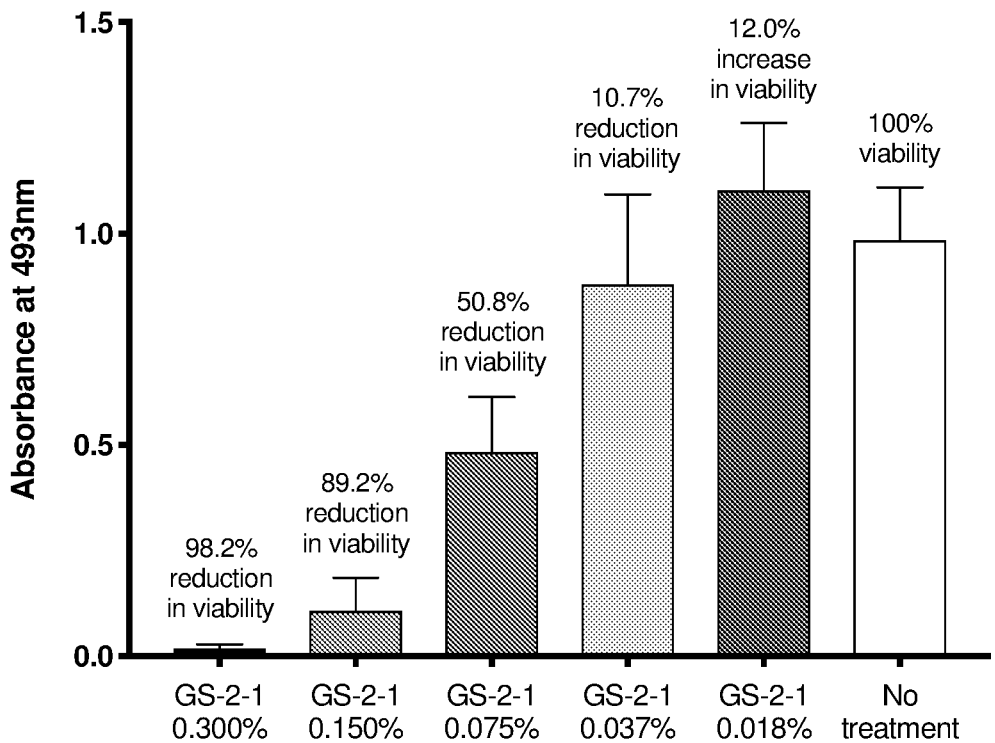
FIG. 33 is a graph showing anti-cancer test results for another example of a mixture of fatty acid and amino acid as described herein, in which the molar ratio of fatty acid:amino acid is between about 1:0.6 and about 1:1.6 (in this example, LARG and Decanoic acid, GS-2) at different concentrations on cultured A549 human lung cancer cells following a 24 hour incubation with various concentrations of the agent.

Similar anti-cancer results were seen using other combinations of amino acid and fatty acid, as mentioned above. For example, FIG. 33 is a graph showing very similar data for GS-2 (a mixture of LARG and Decanoic acid). In FIG. 33, the effect of GS-2 on A549 Human Alveolar Adenocarcinoma cells is shown. At a concentration of 0.300% of GS-2, a 98.2% reduction of viability of the lung cancer cells was seen. As described above for GS-1, A549 human lung cancer cells were seeded onto sterile 96 well plates at 7,000 cells per well. After 24 hours of growth, the cells were further incubated at 37 degrees Celsius with dilutions of GS-2 (from a stock concentration of 30%) for 24 hrs. After incubation, the media and test article were removed and replaced with fresh pre-warmed media. 20 µL of MTS was added to each well containing 100 µL of media and was incubated for 2 hrs. After incubation the plate analyzed on a 96 well colorimetric plate reader. Blank subtraction was performed on all data using 100 µL media and 20 µL MTS absent cells. n=12 wells (3 replicates×4) per treatment. n=70 wells no treatment. Error bars are standard deviation.

Figure 34:
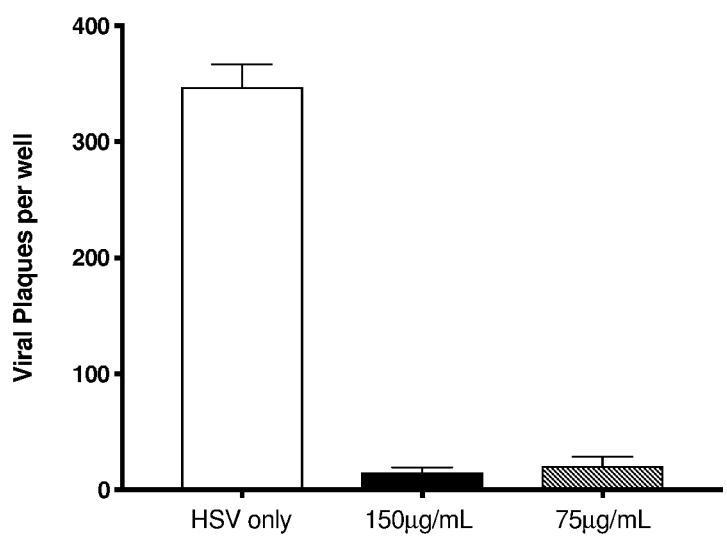
FIG. 34 is a graph illustrating the in vitro anti-viral activity of an example of a therapeutic composition of fatty acid and amino acid as described herein, in which the molar ratio of fatty acid:amino acid is between about 1:0.6 and about 1:1.6 (in this example, LARG and UCA, GS-1) against Herpes simplex viruses (HSV) infected cells at various concentrations.
Figure 35:
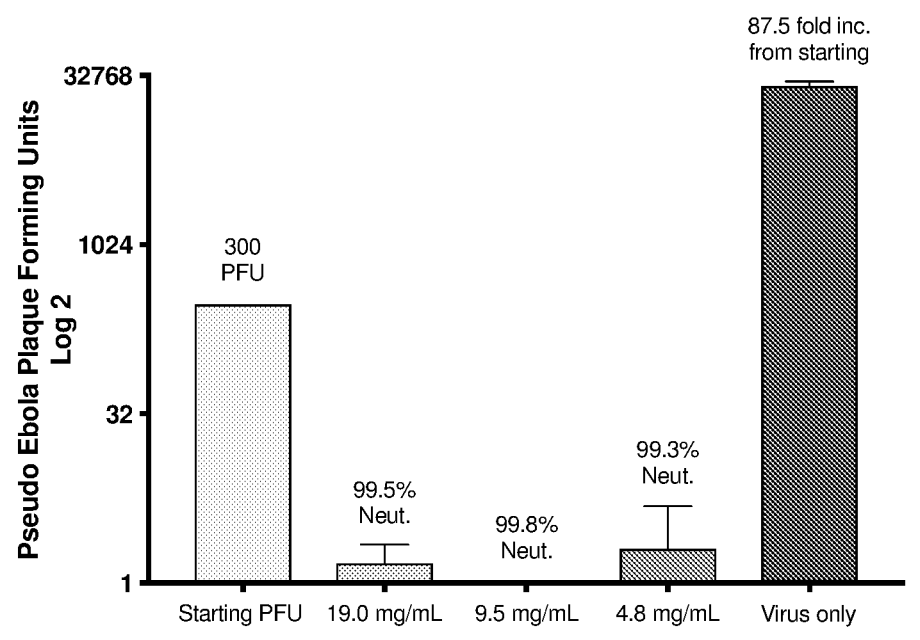

As mentioned, these therapeutic compositions of fatty acid:amino acid in a molar ratio of between about 1:0.6 to about 1:1.6 are also potent anti-viral agents. For example, FIG. 34 is a graph showing the efficacy of these therapeutic compositions against HSV infected cells. In this graph two concentrations of GS-1 are shown against HSV infected cells (150 µg/mL and 75 µg/mL). FIG. 35 shows a similar result against pseudo-Ebola infected cells at three working concentrations of one example of a therapeutic composition of fatty acid:amino acid (e.g., GS-1). Preliminary results show the same effect when these therapeutic compositions are used to treat other viral agents such as influenza and smallpox.

Thus, the compositions described herein were generally effective against bacteria, including both gram-positive and gram-negative bacteria. For example, GS-1 and GS-2 (as well as all other fatty acid:amino acid therapeutic compositions within the specified molar ratio tested) showed active anti-bacterial effects against both gram-positive and gram-negative bacteria. For example, any of the fatty acid:amino acid therapeutic compositions described herein also showed efficacy against Clostridium difficile (C. difficile) (data not sown).

Systemic Safety

Systemic safety studies from rodents have shown that the therapeutic compositions described herein (e.g., therapeutic compositions of fatty acid:amino acid in a molar ratio of between about 1:0.6 to about 1:1.6) are safe at even relatively high concentrations. Thus, these compositions may be given topically and/or systemically to treat a patient in need thereof (e.g., for anti-pathogenic reasons and/or anti-cancer treatments). For example, in one study, one exemplary composition (e.g., GS-1) was administered in a single dose via subcutaneous injection at a dose level of 1.25 mL/kg at full strength, corresponding to 381 mg/kg of API. No side-effects were observed.

In another study, GS-2 was administered in a single dose via subcutaneous injection at a dose level of 10 mL/kg at full strength, corresponding to 3,050 mg/kg of API. No side-effects were observed. GS-2 was also administered once daily for 14 days via subcutaneous injection at a dose level of 5 mL/kg at full strength, corresponding to 1,525 mg/kg of API. No side-effects were observed.

Antimicrobial Coatings and Additives

As mentioned above, the compositions described herein may be used for coatings and/or additives, including material additives e.g., to pain, plastics, etc.). For example, GS-1 was used to coat central venous catheters to provide antimicrobial activity against gram-positive (MRSA) and gram-negative (E. coli) bacteria. In head-to-head testing, GS-1 provided equivalent or better performance than chlorhexidine and silver coatings already used in-market. Coatings may be applied by spraying, dipping, etc. The coatings may be encapsulated, partially encapsulated and/or un-encapsulated.

A therapeutic composition as described herein may also be used as an additive. For example, GS-1 was added to commercially available water-based paint at concentrations of 5% w/w, 10% w/w and 20% w/w to provide antimicrobial activity. At all concentrations, the GS-1 additive successfully eradicated gram-positive (MRSA) and gram-negative (E. coli) bacteria inoculated onto the surface within 24 hours. GS-1 was also added to commercially available plastic (polyurethane) at concentrations of 5% w/w and 10% w/w to provide antimicrobial properties. At both concentrations, the GS-1 additive successfully eradicated gram-positive (MRSA) and gram-negative (E. coli) bacteria inoculated onto the surface within 24 hours.

The methods and compositions described herein may also be used for non-medical/health applications, including for industrial use. In general, these methods and compositions may be used for any process or application in which an amino acid may be used to solubilize a fatty acid. Fatty acids are used for their carbon backbones in a wide range of industrial applications, such as for making nylon. A common problem in working with fatty acids is that they are insoluble and liquid only at high temperatures (thereby requiring lots of energy for heating). The methods and compositions described herein, in which an amino acid, and particularly an amino acid having an electrically charged basic side chain (e.g., Lysine, Histidine, Arginine) may be used to solubilize the fatty acid (e.g., a C4-C40 fatty acid, a C4-C20 fatty acid, a C8-C20 fatty acid, a C8-C18 fatty acid, etc.) in a molar ratio of between about 1:0.6 to about 1:1.6, and may therefore be beneficial any time it is desirable to have a fatty acid in solution.

Dose

In general, any appropriate dose may be used as part of a treatment as described herein. Preliminary work suggests that the compositions described herein may be provided at a dose range that may be effective at very low concentrations (e.g., less than 0.1% w/w), but even higher concentrations may be effective with little, if any side effects. For example, any of the methods described herein may be used to treat a subject within a range of between about 30% w/w and about 0.001% w/w. In some variations the patient may be given a dose of between about 15% w/w and about 0.01% w/w. A patient may be treated with a dose of between about 10% and about 0.01% w/w. A patient may be treated with a dose of between about 5% and about 0.01% w/w. In some variations a patient may be treated with a dose of between about 2.5% and about 0.01% w/w. In some variations, the patient may be treated with a dose of between about 1% and about 0.01% w/w. In some variations the patient may be treated with a dose of between about 0.5% and about 0.001% w/w. In some variations, the patient may be treated with a dose of between about 0.25% and about 0.001% w/w. In some variations, the patient may be treated with a dose of between about 0.25% and about 0.01% w/w.

More than one dose may be provided (e.g., 1× daily, 2× daily, 3× daily, 4× daily, 5× daily, etc. 1 per 36 hours, 1 per 48 hours, 1 per 60 hours, 1 per week, etc.).

Stability

In general, the therapeutic compositions described herein may include a ratio of fatty acid (e.g., undecylenic acid) and amino acid (e.g., L-Arginine) that is stable for storage. For example, compositions of UCA and LARG having a UCA to LARG molar ratio (UCA:LARG) of, e.g., between about 1:0.6 to about 1:1.6 (and particularly about 1:0.65 to 1:1.4, e.g., about 1:0.65 to 1:1.3, about 1:0.65 to 1:1, etc.) may be stable at temperatures above 0 degrees C. for days, weeks or months. Further in some variations, the compositions described herein (e.g., compositions of UCA and LARG) may be stable at even lower temperatures, particularly temperatures such as −20 degrees C., for extended periods of time, e.g., greater than 24 hours (greater than 2 days, 3 days, 4 days, 7 days, 10 days, 14 days, 21 days, 30 days, 60 days, 120 days, 6 months, 1 year, etc.).

In particular, compositions of UCA and LARG having a molar ratio of about 1:1 (e.g. about 1:0.95 by weight) or about 5:4 (e.g., about 1:0.76 by weight) may be especially stable over lower temperatures and longer times. See, e.g., FIG. 19. In FIG. 19 (Table 3), the results of freezer stability (at −20 degrees C. for 24 hours) is shown, showing that the specific molar ratios of UCA to LARG of 1:1 (e.g., 1:0.95 by weight) and 5:4 (e.g., 1:0.76 by weight) exhibited superior stability at lower temperatures as compared to other ratios of UCA:LARG. In FIG. 19, all of the compositions tested may be effective as anti-pathogen and/or anti-cancer compositions, and all of the compositions tested may be stable for extended periods when stored above freezing (e.g., >0 degrees C. for >24 hours), however the UCA:LARG at molar ratios of 1:1 and 5:4 were exceptionally stable. In any of these examples, additional stabilizing agents may be included to enhance stability.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a patient to destroy a Herpes virus pathogen, the method comprising: administering to a patient in need thereof, a therapeutically effective amount of a topical composition including a complex of fatty acid:
   amino acid in a molar ratio of between 1:0.6 to about 1:1.6, wherein the amino acid is L-Arginine and wherein the fatty acid is Undecylenic acid.

2. The method of claim 1, wherein the molar ratio of fatty acid: amino acid is in an approximately 1:1 molar ratio.

3. The method of claim 1, wherein the molar ratio of fatty acid: amino acid is in an approximately 5:4 molar ratio.

4. The method of claim 1, wherein the pH of the composition is between 6 and 10.

5. The method of claim 1, wherein the pH of the composition is between 6.9 and 7.8.

6. The method of claim 1, wherein administering comprises applying the composition to the patient's skin.

7. The method of claim 1, wherein administering comprises spraying the composition on the patient.

8. The method of claim 1, wherein the pathogen is one or more of: a Herpes simplex virus 1, a Herpes simplex virus 2, and a varicella zoster virus.

9. The method of claim 1, wherein the composition further comprises an excipient, diluent, or carrier, excluding cetyl alcohol.

10. The method of claim 9, wherein said excipient, diluent, or carrier is configured for topical application.

11. The method of claim 9, wherein said excipient, diluent, or carrier comprises an emulsifying agent.

12. The method of claim 1, wherein the composition further comprises a cooling or heating additive.

13. The method of claim 1, wherein the composition is configured as a liquid or emulsion in a form suitable for topical administration to a human.

14. The method of claim 1, wherein the composition is configured as an emulsion suitable for topical administration to a human.

15. The method of claim 1, wherein the composition comprises between 0.01 mg/mL and 182 mg/mL of L-Arginine.

* * * * *